United States Patent [19]
Serizawa et al.

[11] Patent Number: 5,830,695
[45] Date of Patent: Nov. 3, 1998

[54] ACTINOMYCETE PROMOTER

[75] Inventors: Nobufusa Serizawa; Ichiro Watanabe, both of Tokyo, Japan

[73] Assignee: Sankto Company, Limited, Tokyo, Japan

[21] Appl. No.: 756,592

[22] Filed: Nov. 27, 1996

[30] Foreign Application Priority Data

Nov. 29, 1995 [JP] Japan .................................. 7-310247

[51] Int. Cl.⁶ .......................... C12P 21/02; C07H 21/04; C12N 1/21; C12N 15/67
[52] U.S. Cl. .................. 435/69.1; 435/189; 435/252.35; 435/320.1; 536/23.1; 536/23.4; 536/23.7; 536/24.1
[58] Field of Search .................. 435/189, 252.35, 435/320.1, 69.1; 530/350; 536/23.1, 23.4, 23.7, 23.2, 24.1

[56] References Cited

U.S. PATENT DOCUMENTS

| | | | |
|---|---|---|---|
| 5,179,013 | 1/1993 | Matsuoka et al. | 435/125 |
| 5,466,590 | 11/1995 | Sariaslani et al. | 435/189 |

FOREIGN PATENT DOCUMENTS

| | | |
|---|---|---|
| 281 245 | 9/1988 | European Pat. Off. . |
| 6-70780 | 6/1994 | Japan . |
| WO 91/10739 | 7/1991 | WIPO . |

OTHER PUBLICATIONS

Database WPI, Section Ch, Week 9133, Derwent Publications Ltd., London, GB; Class B04, AN 91–241722 of JP 03 155 790 A (Yamanouchi Pharm. Co. Ltd.), 3 Jul. 1991.

I. Wantanabe et al, "Cloning, Characterization and expression of gene encoding cytochrome P–450$_{sca-2}$ from Streptomyces carbophilus involved in production of pravastatin, a specific HMG–CoA reductase inhibitor", GENE, vol. 163, 1995, pp. 81–85.

Patel et al. "Phenobarbital & sulfonylurea–inducible operons encoding herbicide metabolizing cytochromes P–450 in Streptomyces griseoius" Gene 112 67–76, 1992.

Purification and characterization of cytochrome P–450$_{sca}$ from Streptomyces carbophilus, Eur. J. Biochem., 184, 707–713 (1989).

*Primary Examiner*—Nancy Degen
*Attorney, Agent, or Firm*—Frishauf, Holtz, Goodman, Langer & Chick, P.C.

[57] ABSTRACT

A 1 kbp length of the 5'-noncoding region of the gene encoding cytochrome P-450$_{sca-2}$ in the actinomycete *Streptomyces carbophilus* has transcription promoter activity which is substrate inducible. When the 1 kbp region is shortened, transcription activity becomes constitutive and the shortened promoters can be used advantageously in expression systems, especially those expressing P-450$_{sca-2}$ in the presence of ML-236B to produce pravastatin sodium.

88 Claims, 4 Drawing Sheets

5,830,695

ACTINOMYCETE PROMOTER

FIELD OF THE INVENTION

The present invention relates to a new form of the transcription promoter associated with the gene encoding a P-450 cytochrome present in *Streptomyces carbophilus*, vectors containing this promoter, the use of such vectors in the expression of proteins, especially P-450$_{sca-2}$, host cells containing such vectors, expression systems comprising such cells and the use of such proteins and expression systems. The present invention further allows industrial scale production of useful proteins using this promoter.

BACKGROUND OF THE INVENTION

In recent years, progress in the field of genetic engineering has made it readily possible to introduce and express foreign genes in various micro-organisms. A particular area of progress has been in respect of *Escherichia coli* (*E. coli*) for use as a host for the production of recombinant proteins, and the resulting techniques are being put into commercial use throughout industry. More recently, considerable progress has been made in research on yeasts as industrial alternatives to *E. coli*.

Actinomycetes (and particularly the genus Streptomycetes) are prokaryotic micro-organisms commonly used in the production of antibiotics. Heterologous DNA is generally introduced into Actinomycetes using a host-vector system developed by Hopwood et al. in the 1980's [c.f. Hopwood, D. A., et al., (1987), "Methods in Enzymology", 153; 116–166, Academic Press, New York]. This technique enabled considerable research and development to proceed on expression vector systems in the Actinomycetes. An example of a transcription promoter useful in Actinomycetes expression vectors is tipA, a promoter inducible by the antibiotic thiostrepton [c.f. Murakami, T., et al., (1989), J. Bacteriol., 171, 1459].

Pravastatin sodium, used in the treatment of hyperlipidemia, has the useful pharmacological effect of being able to reduce serum cholesterol [c.f. Arai, et al., (1988), Ann. Rep. Sankyo Res. Lab., 40, 1–38]. Pravastatin sodium is primarily produced by microbial hydroxylation of ML-236B sodium, a substance produced by the filamentous fungus, *Penicillium citrinum*. The hydroxylation is generally performed in the presence of the actinomycete *Streptomyces carbophilus*. It has been proven that the agent responsible for the hydroxylation activity is a cytochrome of the P-450$_{sca}$ type (hereinafter abbreviated as "P-450sca") [c.f. Serizawa, et al., (1990), Biochimica et Biophysica Acta, 1084, 35–40].

Matsuoka et al. purified a P-450$_{sca}$ cytochrome from *Streptomyces carbophilus* which was capable of catalyzing the hydroxylation of ML-236B sodium at the 6-position. This P-450$_{sca}$ was characterized as occurring in three forms, P-450$_{sca-1}$, P-450$_{sca-2}$ and P-450$_{sca-3}$ [c.f. Matsuoka, et al., (1989), Eur. J. Biochem., 184, 707–713 and EP-A-0 281 245], although it was not established whether these represented isotypes, or products of different genes.

Serizawa et al., cloned and expressed DNA encoding P-450$_{sca-2}$ from *Streptomyces carbophilus* [c.f. Japanese Patent Kokai No. Hei 6-70780 and Watanabe, I., et al., (1995), Gene, 163, 81–85]. The DNA, along with a 1 kbp portion of the 5'-noncoding region of the P-450$_{sca-2}$ gene, was cloned into a multicopy plasmid, pIJ702, and used to transform *Streptomyces lividans* TK21. The transformed *Streptomyces lividans* TK21 converted ML-236B to pravastatin sodium even faster than *S. carbophilus*, thereby demonstrating that the 1 kbp fragment contained strong promoter activity. The 1 kbp 5'-noncoding region was not sequenced.

At the same time, it was also established that expression of P-450$_{sca}$ is subject to substrate induction of transcription, that is, ML-236B and phenobarbital were found to enhance expression of P-450 by as much as 30-fold. This was established by Northern blotting, which found no transcription in the absence of ML-236B, but which found three transcripts when ML-236B sodium was present. The levels of transcription increased over a period of six hours to a maximum rate when in the presence of a substrate.

The DNA encoding P-450$_{sca-2}$ is 1233 bp long, while the promoter region is very nearly the same length, being 1013 bp long, making transformation considerably more difficult than if only the Open Reading Frame (ORF) were being used for the transformation. However, reducing the length of such a complex, substrate-induced promoter would be exceedingly likely to render the promoter useless. In addition, transformation of a host with a vector containing both the ORF and the 1 kbp region has already successfully been performed, so that no need to shorten the ORF or the 5'-noncoding region was perceived.

However, the time lag of six hours until maximal production of P-450 is reached remains a problem, this time lag being a major problem in industrial applications.

OBJECT OF THE INVENTION

Thus, it is an object of the present invention to provide a transcription promoter for a protein to be expressed in an actinomycete which allows significant expression of the protein in a suitable expression system without transcription having to be induced by a substrate for the protein.

It is a further object of the present invention to provide a transcription promoter for a protein to be expressed in a streptomycete which allows significant expression of the protein in a suitable expression system without having to be induced by a substrate for the promoter.

It is a further object of the present invention to provide a transcription promoter for a protein to be expressed in an actinomycete which allows constitutive expression of the protein in a suitable expression system without having to be induced by a substrate for the promoter.

It is a yet further object of the present invention to provide: a DNA sequence for all or part of such a promoter; DNA having all or part of the activity of such a promoter; vectors comprising such promoters; host cells transformed by such vectors; and processes for producing recombinant protein using such host cells.

It is a particular object of the present invention to provide a process for producing pravastatin sodium by using a host expressing a recombinant P-450 protein whose transcription is controlled by such a promoter.

Other objects and advantages of the present invention will become apparent in the following description.

SUMMARY OF THE INVENTION

We have now discovered that a reduction in the length of the 5'-noncoding region associated with the gene encoding P-450$_{sca-2}$ surprisingly not only removes the substrate enhancing effect of ML-236B, but also increases the effectiveness of the promoter.

Thus, in a first aspect, the present invention provides DNA having transcription promoter activity, said DNA corresponding to a part but not all of a 1 kbp 5'-noncoding region immediately adjacent an open reading frame of *Streptomyces carbophilus,* said open reading frame encoding a P-450 cytochrome.

The DNA particularly preferably has transcription promoter activity in at least one strain of *Streptomyces carbophilus* and/or in at least one strain of *Streptomyces lividans.*

DETAILED DESCRIPTION OF THE INVENTION

Figure 1:
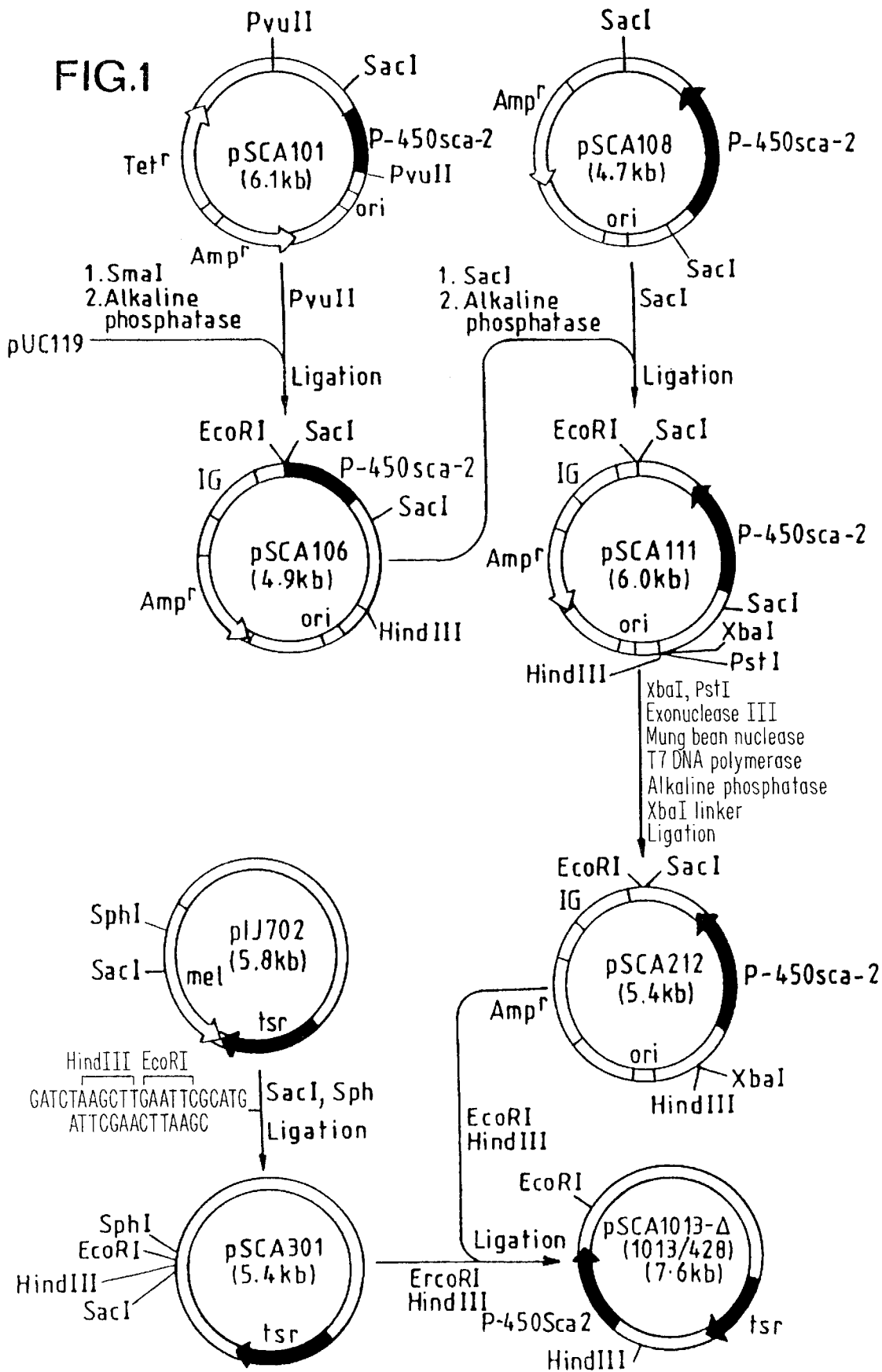
FIG. 1 is a plan for the construction of a plasmid, pSCA1013-Δ(1013/428), containing 428 bp of the 5'-noncoding region of the P-450$_{sca-2}$ gene.

Essentially, the present inventors have established that reducing the size of the 5'-noncoding region associated with a P-450 gene of *S. carbophilus,* particularly the 5'-noncoding region associated with the P-450$_{sca-2}$ gene, has little or no effect on the maximal rate of transcription promotion, and that the reduction in size also advantageously removes the requirement for substrate induction. The effect of substrate induction is a positive effect, so that removing this effect would be expected to leave a promoter which only promoted transcription at a basal level. Instead, the shortened promoter regions perform significantly better than the basal level associated with the 1 kbp promoter. Even lengths as short as 74 bp still have advantageous activity compared with the 1 kbp promoter.

Furthermore, the transcription rate of the reduced length promoters appears to be constitutive, so that high rates of transcription are achieved immediately, instead of having to wait for maximal rates of expression to occur over a period of six hours after exposure to ML-236B, or another appropriate substrate. This is particularly important in industry.

The 1 kbp 5'-noncoding region having transcription promoter activity and which is immediately adjacent a P-450 ORF is also referred to herein as the 5' promoter. In particular, we prefer that it be the promoter associated with the P-450$_{sca-2}$ gene of *S. carbophilus.*

Although the 5' promoter is referred to as being of a length of 1 kbp, this is only the approximate length of a region extending 5' from the transcription start region (tsr) of the ORF. The tsr is located at about position 384 of SEQ. ID. NO. 1, and the ATG initiation codon immediately follows position 428. The end of the region containing the 5' promoter is the SacI site located 1013 bp upstream of the ORF. The SacI site of this region was described by Watanabe et al. (supra), who did not determine the length of the 5' promoter. For ease of reference, the 5' promoter is referred to herein as being 1 kbp long, rather than 1013 bp, as this is very substantially correct and does not form an essential feature of the present invention, as will become more clear hereinunder. In any event, the promoters of the present invention must be shorter than the full 1013 bp length of the 5' promoter.

The 1 kbp 5' region adjacent the P-450$_{sca-2}$ gene does not necessarily contain the entire promoter region for this gene, although the size of the region is suggestive that it does. In fact, the promoter does not appear to occupy a well-defined region, owing to the fact that we have established that a region as small as 74 bp in length still has comparable, or better, activity than the original 1 kbp 5' promoter. However, it is also the case that the promoters of the present invention have considerably better promoter activity when they have in excess of about 160 bp, preferably 300 bp, or more.

The DNA's of the present invention, also referred to herein as the promoters of the present invention, correspond to the 1 kbp 5' promoter, provided that they are shorter than the 5' promoter's 1 kbp length. The reduction in length can be effected by any suitable means, such as the removal of portions by means of restriction endonucleases, by engineering specific, but shorter, sequences, or by digestion from either the 3' or 5' end of the sequence, said means including combinations of the foregoing.

It will be appreciated that the promoters of the present invention must generally be double stranded (ds) in order to exhibit promoter activity, although it will be appreciated that the present invention also envisages either of the complementary strands making up the promoters of the invention. The present invention further extends to portions of the promoters of the invention, or portions of either or both of the complementary strands which can ultimately be used to construct a promoter of the invention.

We have particularly found that 5' digestion yields excellent results, so that even a 74 bp portion located at the 3' end of the promoter sequence still has superior activity. Accordingly, in a preferred embodiment, the DNA of the present invention corresponds to the 5' promoter partially digested in the 5'→3' direction. There is no minimum length of promoter DNA, provided that the DNA still possesses the requisite promoter activity.

Although good promoter activity is seen at promoter lengths of less than 100 bp, especially at the 3' end, there appears to be a significant improvement in activity at lengths between 158 and 320 bp. The 320 bp fragment has promoter activity of around 5× greater than the 158 bp fragment. Both fragments are 3' terminal fragments of the 1 kbp 5' promoter. This difference in promoter activity is not crucial to the present invention, owing to the fact that a length of 152 bp (the difference in the two lengths) has minimal effect on transformation or expression.

If the person skilled in the art desired to identify the precise length of promoter where the transition between greater and lesser activity occurred, then the necessary procedure would be entirely straightforward and readily apparent to the skilled person. However, there can be no advantage in the identification of such a length, as there is no practical difference nor advantage to be gained between using 158 bp and 320 bp as a promoter sequence.

It will be appreciated that it is generally preferred to use a promoter with significantly higher activity, rather than lower activity, so that maximum transcription can be achieved. However, it may be that the rate of transcription using a promoter with higher activity is undesirably high, and that too much of the host's resources are being exhausted in protein manufacture. In such a case, a less active promoter would be desirable.

We have also established that there is a length of promoter somewhere between 428 bp and the full 1 kbp, where the dependence on substrate induction is lost. Although this specific length of 428 bp was obtained by 5' terminal digestion, it is entirely possible that any 428 bp sequence, or similar, within the overall 1 kbp sequence may equally serve as a promoter.

As described above, the loss of the dependence on substrate induction is highly advantageous. However, at the same time, the precise length at which this happens is not important. We demonstrate that the activity of a promoter having a length of 428 bp is equivalent to, or slightly higher than, the full activity of the 1 kbp 5' promoter, at least after substrate induction for one hour. Thus, a promoter of less than half the length of the original promoter works at least as well as the original, but without the requirement for substrate induction. This means that any process in which the rate of expression is a factor is immediately advantaged. Lengths of greater than 428 bp become increasingly unwieldy, without benefiting the user. In addition, at some point, the longer promoters also become subject to substrate induction once again, thereby negating any advantage gained by the shorter promoters of the present invention.

Accordingly, the DNA of the present invention is preferably of such a length that it demonstrates promoter activity substantially equivalent to, or greater than, that of the 320 and/or the 428 bp 3' fragments of the 5' promoter. In particular, we prefer that the length of the promoter should not be so long that it is subject to substrate induction.

The term "substrate induction" is well known in the art. Essentially, certain expression products are frequently only required in nature when a certain substrate is present on which they can act. In the absence of said substrate, the organism would be wasting resources by expressing the product. Accordingly, various systems have evolved in nature so that expression of the product only occurs in the presence of the substrate.

In the case of the $P-450_{sca-2}$, this is achieved by a substrate, such as ML-236B, acting at the promoter site to induce mRNA transcription. It is by no means certain that ML-236B is the natural substrate for the $P-450_{sca}$ cytochromes. There may well be other substrates, including any which are the intended substrates, if these are different from ML-236B, which can induce the 5' promoter. A further example of a suitable substrate to induce the 5' promoter is phenobarbital, as described above. However, the precise nature of the inducer for the 5' promoter is not important to the present invention, and will not be discussed further herein.

Although the present invention is not bound by theory, it seems likely that, surprisingly, the induction of the $P-450_{sca-2}$ cytochromes by the substrate somehow overcomes a block on transcription. Reduction in the size of the 1 kbp promoter region, especially by digestion of the 5' end of the promoter, then seems to serve to remove the block. For this reason, we believe that there is no particular length of promoter at which substrate induction resumes, rather that promoter activity decreases with increasing length, after a certain point, as the transcription promotion block is regenerated. Substrate induction may begin to be effective in a manner directly proportional to the regeneration of the transcription promotion block, or may only be possible once a certain length is reached. In any event, promoters with unreduced activity owing to increased length beyond about 500 bp are preferred. In other words, promoters which have a length in excess of about 500 bp, more particularly in excess of 428 bp, and which show a reduction in activity, are not preferred.

The DNA of the present invention corresponds to a part, or parts, of the 5' promoter. By the term "corresponds" it is meant that the DNA of the invention has a similar type of promoter activity to that of the 5' promoter, in that it can serve to promote transcription of a $P-450_{sca}$ cytochrome ORF. The level at which such promotion occurs is not an essential feature of the present invention, and levels of promoter activity of the promoters of the present invention are described herein. The only requirement is that the promoters of the present invention have activity which is, in some way at least, better than that of the 5' promoter, as described herein.

The promoters of the invention may correspond directly to a part or parts of the 5' promoter. In a simple embodiment, the 5' promoter may be digested from the 5' end, so that the resulting promoter of the invention has the same sequence as the remaining 3' portion of the 5' promoter. If the 5' promoter is digested from the 5' end and a portion is also removed by endonuclease digestion and ligation, then the resulting promoter of the invention will correspond directly to the relevant two parts of the 5' promoter. In both of these examples, the resulting promoter has identical sequences to one or more portions of the 5' promoter.

The promoter of the present invention will generally have one or more similar or identical sequences to that or those of the 5' promoter. However, the nucleotide sequence of the promoters of the invention need not correspond directly to those of the 5' promoter. Although it is generally preferred that the promoters of the invention share very substantial sequence homology with the relevant portions of the 5' promoter to which they correlate, this is not essential. The only requirement is that the requisite promoter activity is shown.

The promoters of the present invention can vary as much as is desired from the original 5' promoter, provided that the resulting promoter still exhibits the requisite promoter activity. In general, there will be little advantage to be gained by varying the sequence, and there is no guarantee that altering the base sequence will achieve anything other than to destroy or diminish promoter activity. However, a certain amount of modification of the base sequence is unlikely to have any significant effect, especially as it is not required for the base sequence to encode a protein.

Modifications to the base sequence will generally occur through the transformation procedure, or be made for convenience, such as to introduce a restriction site, for example. Thus, the present invention envisages promoters which vary from that part, or those parts, of the 5' promoter sequence to which they correlate by, for example, deletions, inversions, insertions and substitutions. Variations on the naturally occurring 5' promoter sequence may also occur in nature, and promoters of the invention based on such variants are also envisaged.

Other differences and alterations in the sequence and means for effecting them will be readily apparent to those skilled in the art, and the present invention envisages all of these. The promoters of the present invention which vary in such a way, other than by natural variation, are also referred to herein as mutants, so that both mutants and variants are envisaged. However, it will be appreciated that the expression, "corresponding to a part but not all of a 1 kbp 5'-noncoding region immediately adjacent an open reading frame of *Streptomyces carbophilus*, said open reading frame encoding a P-450 cytochrome" encompasses such mutants and variants.

As a general rule, suitable mutants and variants can hybridize at 60° C. in 6×SSC with DNA having the nucleotide sequence 1 to 428 of SEQ ID NO. 1 of the sequence listing. The DNA to which the mutants and variants hybridize may or may not form part of a longer sequence.

As has been discussed, the promoters of the present invention exhibit superior activity to the 1 kbp 5' promoter. This does not necessarily mean that the level of transcription of the ORF subject to promotion by a promoter of the invention is higher than that promoted by the 1 kbp 5' promoter when induced by substrate. Instead, it is often the case that constitutive promotion by a promoter of the invention serves to ensure that levels of protein activity are still higher after a period of one hour, for example, than compared with those obtained with the 5' promoter after one hour of substrate induction. Such constitutive production can be far preferable to a slow build-up, which then reaches levels beyond those which are either required or useful, for example.

Although the DNA's of the present invention are advantageously useful with the P-450$_{sca}$ cytochromes, it will be appreciated that they can be used in combination with any suitable sequence to be expressed in any suitable prokaryote host. In particular, the promoters of the present invention may be used in suitable actinomycete hosts, especially streptomycetes. The promoters of the invention correspond to part or parts of a promoter derived from *S. carbophilus*, so that requisite promoter activity is shown if a promoter of the invention is capable of promoting transcription of a P-450$_{sca}$ cytochrome ORF.

From the foregoing, it will be appreciated that there are further provided promoters of the invention when operatively linked to a suitable ORF. There are also provided vectors, such as plasmids, containing the promoters of the invention, especially when the promoter is operatively associated with an ORF, and hosts containing such vectors.

The vectors need not necessarily be expression vectors. Such other vectors may be used to multiply the promoters of the invention, or to provide a readily accessible library. However, expression vectors are preferred, and expression systems comprising a host and an expression vector of the invention are particularly preferred.

It is currently preferred to employ *S. lividans* when an actinomycete is used as a host cell for the expression of products from heterologous DNA. In the case of P-450$_{sca}$ cytochromes, especially P-450$_{sca-2}$, *S. lividans* also expresses the necessary electron transfer system to permit the cytochrome to take part in the hydroxylation of ML-236B. However, any other suitable protein or expression product may also be expressed via an expression system containing a promoter of the invention.

It is not generally preferred to express eukaryotic DNA in prokaryotes, such as *S. lividans*, as certain post-translational events do not take place in prokaryotes which occur naturally in eukaryotes, such as glycosylation. However, this does not prevent expression of eukaryotic products in systems of the present invention, provided that it is understood that any required post-translational modifications not naturally occurring in the expression system will not take place, unless specifically catered for.

Expression systems of the present invention are especially useful for expressing prokaryotic expression products in large amounts. Expression products can be produced in even larger quantities, if multicopy plasmids, such as pIJ702, are used in the expression system.

Expression systems of the present invention are more particularly useful for the expression of products which are normally only expressed after substrate induction. Such systems can be used in processes for the production of certain substances, such as antibiotics. Such processes are possible, for example, when the expression product has activity to convert a substrate into a final product, or into a later stage intermediate, or even to break down a substrate. Such a process may involve co-culture of the expression system, if appropriate, with a system producing the substrate to be acted upon.

In the circumstance where the product of the expression system of the invention is normally substrate induced, then co-cultivation with the substrate producing expression system would normally be subject to time lag, so that it is necessary to wait for the expression system to produce sufficient expression product. Using the expression systems of the present invention, this is no longer a problem, as the product is automatically synthesized by the system, without the necessity for substrate induction, thereby eliminating the time lag factor.

It will be appreciated that the expression systems of the present invention are particularly applicable to the expression of P-450 cytochromes, especially P-450$_{sca}$ cytochromes and most especially the P-450$_{sca-2}$ cytochrome. P-450$_{sca-2}$ is expressed by *S. carbophilus*, as described above, and *S. carbophilus* is advantageously co-cultivated with *Penicillium citrinum* in the production of pravastatin sodium. In this system, P-450$_{sca-2}$ serves to hydroxylate the substrate ML-236B expressed by *Penicillium citrinum*, but only after a delay while ML-236B induces transcription of P-450$_{sca-2}$. Using an expression system of the present invention, it is no longer necessary to have a lag period in the production of pravastatin sodium, and this leads to great advantages in the industrial production of pravastatin sodium.

Some preferred embodiments of the present invention are as follows.

Preferred promoters of the present invention hybridize with DNA having the nucleotide sequence 1 to 428 or 1 to 320 of SEQ ID NO. 1.

Promoters having the nucleotide sequence 1 to 428 of SEQ ID NO. 1 are preferred. Promoters having the nucleotide sequence 1 to 320 of SEQ ID NO. 1 are also preferred. The present invention further provides mutants and variants of such promoters.

Also provided are recombinant DNA vectors comprising promoters of the invention, particularly where such vectors further comprise DNA encoding a desired polypeptide under the control of the promoter, and wherein the vector is capable of expressing the polypeptide in an appropriate host cell. It is preferred that the polypeptide is cytochrome P-450$_{sca-2}$.

The invention also provides host cells transformed by such vectors. Preferred host cells are actinomycetes, particularly *Streptomyces lividans*. Particularly preferred is *Streptomyces lividans* SANK 62795 (FERM BP-5299).

The present invention further provides a process for producing a desired polypeptide, such as is defined above, the process comprising culturing a transformed host cell, as defined above, under conditions permitting production of the polypeptide to produce the polypeptide, and recovering the polypeptide.

The present invention further provides a process for producing pravastatin sodium which comprises culturing *Streptomyces lividans* strain TK21 transformed by an expression vector of the invention encoding P-450$_{sca-2}$, in a medium containing ML-236B sodium, and under conditions allowing the production of cytochrome P-450$_{sca-2}$, and allowing ML-236B sodium to be converted to pravastatin sodium in the transformed cells by the catalytic action of cytochrome P-450$_{sca-2}$ produced therein, and then recovering the pravastatin sodium from said transformants and/or said medium. It is preferred that the transformed strain is *Streptomyces lividans* SANK 62795 (FERM BP-5299). It is also preferred that the ML-236B is produced by *Penicillium citrinum* which is co-cultivated with said strain.

The 5' promoter is not homologous with any known promoter, whether from an actinomycete, or any other source. In common with other promoters, the promoters of the invention cause the initiation of transcription of DNA coding for a protein or a polypeptide into mRNA. This is the first part of the intracellular biosynthesis of proteins or polypeptides (which terms are used interchangeably herein). Thus, the promoters of the invention are transcription promoters, this function being referred to as transcription promoter activity. The 5' promoter, as well as the promoters having the 428, 320, 158, 101 and 74 bp sequences of SEQ. ID no. 1, all have this activity.

It will be appreciated that the promoters of the present invention may have one or more additional base pairs linked in tandem, upstream and/or downstream. Such additional sequences are only limited in that no substantial amount of substrate induction should be re-introduced, and also that a useful amount of promoter activity should be retained.

Polypeptides under the control of the promoters of the invention may be as described above. It will be appreciated that they may have any amino acid sequence, such as, for example, that of: a natural, variant or polymer form of a novel or known protein; a fused form of two or more different proteins; or a newly designed polypeptide. As described above, the preferred polypeptide is cytochrome P-450$_{sca-2}$.

With regard to vectors, it will be appreciated that the vector to be transformed should be one that is capable of self-replication in a suitable host cell. Thus, the vector should contain a self-replication sequence, or replicon. In the case of actinomycetes, a preferred such vector is pIJ702.

With regard to the host, there is no particular limitation, other than it be suitable for the vector chosen. In general, any host cells can be used, such as those collected from the wild, or that can be acquired by purchase or transfer. Preferred host cells are Actinomycetes, preferably *Streptomyces carbophilus* or *Streptomyces lividans*, and, most preferably, *Streptomyces lividans* strain TK21.

In a process for the production of pravastatin sodium, such as defined above, comprising culturing a transformed strain of *Streptomyces lividans* in the presence of ML-236B sodium, the resulting pravastatin sodium can be recovered by known methods.

In a straightforward embodiment, the promoters of the present invention may be obtained by cloning the DNA from *Streptomyces carbophilus*, using the methodology of Watanabe, et al. [Gene, (1995), 163, 81–85]. A preferred strain of *Streptomyces carbophilus* from which the promoters of the invention can be cloned is *Streptomyces carbophilus* SANK 62585 (FERM BP-1145).

In the present embodiment, a genome library may be prepared from the whole genomic DNA of *Streptomyces carbophilus*, using pUC18 (obtainable from Takara Shuzo Ltd., Japan), for example, as a cloning vector. It will be appreciated that such libraries and vectors form a part of the present invention. An oligonucleotide probe may then be synthesized based, for example, on the predicted N-terminal amino acid sequence of P-450$_{sca-2}$. This oligonucleotide probe may then be used to identify a clone from the library encoding at least a part of P-450$_{sca-2}$ As the N-terminal of a protein is encoded by the 5' end of the ORF, then it is likely that any clone identified by this method will also have a significant amount of 5' untranslated and noncoding region, which is where the 5' promoter is located. A suitable screening method using the library and the oligonucleotide probe is the colony hybridization method [c.f. Maniatis, T. et al., (1982), "Molecular Cloning—A Laboratory Manual", Cold Spring Harbor Laboratory, New York—any methods referred to herein which are not accompanied by any specific reference will generally be described in "Molecular Cloning—A Laboratory Manual"].

Even if the clone identified by this, or any other, method only contains a portion of the promoter of the present invention, then a full clone can still be obtained. A labelled probe can be prepared from the clone containing only a portion of the desired DNA. This labelled probe can then be used as a template for a further screening of the genome library, in order to identify and isolate a clone containing at least as much of the 5' promoter as is required.

It will be appreciated that the present invention envisages the isolation of a clone comprising either the whole of the 5' promoter or only a part of the 5' promoter. If the whole sequence is obtained, then this can be further processed, such as by sub-cloning, in order to obtain a promoter of the present invention. If a partial sequence is obtained, then this may also be further processed, as with the whole sequence, or may suffice as a promoter of the invention without any substantial change in its sequence.

It will further be appreciated that the above suggested method for the cloning and preparation of a promoter of the present invention is not the only method which can be used, and that other suitable methods will be readily apparent to those skilled in the art. Any of the steps, or even the whole methodology, may be changed. For example, rather than use a probe corresponding to the N-terminal sequence of P-450$_{sca-2}$, a probe prepared from the 3' end of the 5' promoter can be used. Vectors are not particularly limited, and any suitable cloning vector may be used, such as other commercially available vectors, including pBR322.

In accordance with the present invention, it will also be appreciated that the promoters of the present invention may be chemically synthesized, using the information given in SEQ. ID no. 1. If promoters of the present invention are to be chemically synthesized, then this may be performed, for example, by the phosphite triester method [c.f. Hunkapillar, M., et al., (1984), Nature, 310, 105–111]. It is also possible that semisynthesis may be employed, for example, using a combination of cloning techniques and engineering using the information given herein. Suitable methods of such semisynthesis are well known in the art.

Returning to the originally described method of obtaining a promoter of the present invention by screening a library, promoter DNA can be obtained from the clone containing the desired sequence by methods well known to those skilled in the art [c.f. Maniatis, T. et al., (1982), supra]. For example, the plasmid DNA fraction can be isolated and the promoter DNA can be isolated from the plasmid DNA, such as by using one or more restriction enzymes.

The preferred strain serving as the source for the 5' promoter is *Streptomyces lividans* SANK 62795. This strain was deposited in accordance with the terms of the Budapest Treaty for the Deposit of Micro-organisms on Nov. 21, 1995, at the National Institute of Bioscience and Human Technology Agency of Industrial Science and Technology, under accession number FERM BP-5299. *Streptomyces lividans*

SANK 62795 is an actinomycete containing the recombinant DNA vector pSCA1013-Δ(1013/428) which, in turn, contains DNA having transcription promoter activity and which consists of the nucleotide sequence 1 to 428 of SEQ ID NO. 1 of the sequence listing, together with DNA encoding the cytochrome P-450$_{sca-2}$, the plasmid being able to produce the protein in the actinomycete cells through the activity of the 428 bp promoter.

In the appended Sequence Listing, the source of SEQ. ID NO. 1 is given as *S. carbophilus* SANK 62585 having the accession no. FERM BP-1145. This was the original source of the 1 kbp 5' promoter, to which the shorter promoters of the present invention correspond, and was deposited with the Fermentation Research Institute Agency of Industrial Science and Technology in accordance with the terms of the Budapest Treaty for the Deposit of Micro-organisms on 5 Sep. 1985.

Both *S. lividans* 62795 and *S. carbophilus* 62585 are typical examples of *S. lividans* and *S. carbophilus*, respectively, and can be cultured as described in Hopwood, D. A., et al., (1985), "Genetic Manipulation of Streptomyces: A Laboratory Manual", The John Innes Foundation, Norwich, UK, which also describes typical physical attributes for these strains. These two strains can be selected for resistance to thiostrepton.

In accordance with a preferred embodiment of the present invention, a transcription promoter having the nucleotide sequence 1 to 428 of SEQ ID NO. 1 of the sequence listing is isolated by culturing *Streptomyces lividans* SANK 62795, followed by recovering pSCA1013-Δ(1013/428) from the cells and digesting the plasmid with restriction enzymes.

If desired, the nucleotide sequence of any cloned DNA can be determined by, for example, the Maxam-Gilbert chemical modification method [c.f. Maxam, A. M., and Gilbert, W., (1980), Methods in Enzymology, 65, 499–599] or the dideoxy chain termination method using the M13 phage [c.f. Messing, J., and Vieira, J., (1982), Gene, 19, 269–276].

If it is desired to establish whether a specific DNA sequence hybridizes with DNA containing all or part of the nucleotide sequence 1–428 of SEQ ID NO. 1 of the sequence listing, then this may be determined as follows.

Specifically, the DNA to be tested is first electrophoresed on an agarose gel as necessary. The DNA is then blotted on a film of nitrocellulose or nylon, followed by fixing the adsorbed DNA onto the film by heat treatment or ultraviolet irradiation. A probe is then used. The probe has the desired length of nucleotide sequence 1 to 428 of SEQ ID NO. 1, and is labelled with, for example, a radioactive isotope, such as $^{32}$P, biotin, digoxigenin or an enzyme, and is typically prepared in accordance with either the random primer method [c.f. Feinberg, A. P., et al., (1983), Anal. Biochem., 132, 6–13] or the nick translation method [c.f. Maniatis, T., et al., (1982), supra].

The nitrocellulose or nylon film is immersed in hybridization solution containing the probe and is then incubated at a suitable, predetermined temperature, such as 60° C. Following incubation, the film is washed and the probe can be detected using methods appropriate to the label used.

The hybridization solution will normally contain SSC (saline-sodium citrate; 1×SSC contains 0.15M sodium chloride and 15 mM sodium citrate in deionized water). The concentration of SSC in the hybridization solution is preferably 4–8×SSC, more preferably 6×SSC. The incubation temperature is preferably from 30° to 70° C., and is more preferably 60° C.

DNA hybridizing with DNA having all or part the nucleotide sequence 1 to 428 of SEQ ID NO. 1 of the sequence listing, may be cloned from various genome libraries by the method described. It will be appreciated that more promoters of the present invention will hybridize with DNA having the 428 sequence rather than the 320 or other shorter sequences, but the length of the sequence chosen for the hybridization experiments can readily be selected by those skilled in the art using the information given herein.

As previously described, DNA obtained in this manner may be artificially modified by methods well known in the art, such as by substituting, deleting or inserting one or more nucleotides at a desired site by, for example, site specific mutagenesis [c.f. Mark, D. F., et al., (1984), Proc. Natl. Acad. Sci. U.S.A., 81, 5662–5666]. It will be understood that the present invention extends to such DNA, provided that it possesses the requisite transcription promoter activity.

In order to confirm that the DNA obtained as described above has transcription promoter activity, a vector containing the DNA tandemly linked to an ORF is constructed and expressed in a suitable host. To start, (i) a recombinant DNA vector is constructed, wherein DNA encoding a suitable protein is operatively ligated with the putative promoter DNA and inserted into a suitable vector, such as actinomycete plasmid pIJ702 [c.f. Katz, E., et al., (1983), J. Gen. Microbiol., 129, 2703–2714], and then (ii) a suitable host cell, which allows the vector to stably replicate, such as *Streptomyces lividans* in the case of a vector constructed from pIJ702, is transformed with the vector, the level of expression of the protein encoded by the coding DNA then being established.

In the above technique, transformation can be carried out in accordance with Hopwood, et al., [c.f. Hopwood, D. A., et al., (1985), "*Genetic Manipulation of Streptomyces: A Laboratory Manual*", The John Innes Foundation, Norwich, UK] when the transformant is, for example, a streptomycete. It will be appreciated that the gene used to assay promoter activity should not usually be present or expressed in the host, prior to transformation.

Levels of transcription can be readily established by Northern blotting, for example. In Northern blotting, or Northern hybridization [c.f. Maniatis, T., et al., supra], the host cell is cultured after transformation. The RNA is then extracted and purified from the cell and subjected to agarose gel electrophoresis, and the RNA is then blotted onto a film of nitrocellulose or nylon, for example. A probe (DNA, RNA or synthetic oligonucleotide) can be labelled with a radioisotope, such as $^{32}$P, biotin, digoxigenin or with an enzyme specifically detecting the gene for the protein. This probe can then be used to detect the mRNA transcribed from the gene, by hybridization.

Levels of transcription can also readily be determined by RNA-PCR [Polymerase Chain Reaction, c.f. Innis, M. A., et al., (1990), "PCR PROTOCOLS", Academic Press, New York]. The RNA is first prepared in a manner similar to that for Northern hybridization. cDNA is then synthesized, using reverse transcriptase, from the mRNA, which acts as the template. Reverse transcription may use, as a primer, either oligo(dT), which tends to be rather non-specific, or an oligonucleotide having a sequence homologous to a portion of the gene encoding the protein to be expressed. Using this cDNA as a template, a polymerase chain reaction can be performed by using two oligonucleotide primers. The primers are complementary to opposing strands of the ORF, and the sites with which they are complementary have separate locations within the gene, so that the strands generated by PCR are able to hybridize with each other. After the reaction has been allowed to proceed for a given amount of time, the resulting dsDNA is electrophoresed and detected on nitrocellulose, for example, to determine the level of transcription of the desired DNA, based on the presence or absence of a band of the expected length.

Levels of expression of the product may be established by determining the physiological activity of the protein produced. Thus, for example, a recombinant DNA vector may be prepared, wherein DNA encoding a protein with a given activity, such as an enzyme, is operatively connected, such as by ligation, to the 3'-terminal of the putative promoter. Levels of expression of the ORF connected to the putative promoter can then be assayed in a manner appropriate to the expression product.

In the instance where such a plasmid encodes the cytochrome $P-450_{sca-2}$, and the plasmid is compatible with *S. lividans*, then the plasmid can be introduced into a strain of *Streptomyces lividans* not producing $P-450_{sca-2}$, and the transformant can then be cultured in the presence of ML-236B sodium. The amount of pravastatin sodium produced is then indicative of the level of expression of $P-450_{sca-2}$ as promoted by the putative promoter.

It will be appreciated that methods for assaying expression products may be tailored specifically to the relevant products. For example, the putative promoter may be operatively linked to a drug-resistance gene, such as a chloramphenicol acetyl transferase gene [c.f. Gorman, C. M., et al., (1982), Mol. Cell. Biol., 2, 1044–1051], or to a luciferase gene [c.f. de Wet, J. R., et al., (1987), Mol. Cell. Biol., 7, 725–7371,] which can be detected by methods well known in the art. Other methods for assaying expression via the activity of the expression product may also be employed.

Another method for measuring expression, for example, is by way of recognizing the product using an appropriate antibody. Once again, an expression vector containing the putative promoter operatively linked to the ORF is prepared and transformed into a suitable host and cultured under suitable conditions for expression. The culture medium, or an homogenate of the transformed cells, is exposed to the antibody, and the amount of antigen-antibody complex is measured. Suitable measurement techniques include radioimmunoassay [c.f. Berson, R. S., et al., (1973), "Methods in Investigative and Diagnostic Endocrinology", Vol. 2A, 2B, North-Holland Publishing Co., Amsterdam], enzyme immunoassay [c.f. Engvall, E., (1980), Methods in Enzymology, 70(A), 419–439], Western blotting [c.f. Harlow, E., et al., (1988), "Antibodies—A Laboratory Manual", p. 471, Cold Spring Harbor Laboratory, New York] and immunoprecipitation [c.f. Kessler, S. W., et al., (1981), "Methods in Enzymology", 73(B), 442–459], depending on how it is desired to measure the interaction, and on whether the antibody or antigen is labelled in any way. In any event, it will be appreciated that the present discussion of these techniques is not exhaustive, and other methods will be readily apparent to those skilled in the art.

It will also be appreciated that many other methods for determining transcription promoter activity of putative or actual promoters of the present invention will be readily available and apparent to those skilled in the art, and that the present invention embodies all such methods. For example, where the protein to be expressed has a characteristic property other than activity or antigenicity, methods determined by such a property can also be used to assay, directly or indirectly, such activity.

Once it has been established that DNA intended for use as a promoter of the present invention has the necessary activity as a promoter, then it may be employed to construct an expression vector for any suitable, desired protein. Any appropriate host may be used for this purpose, and the host may or may not be the same as the host which was used to establish whether the DNA actually had promoter activity. The protein is not restricted as to its sequence, and may have any amino acid sequence. As described above, such sequences may be selected from, but are not limited to: a natural, variant or polymer form of a novel or known protein (or a peptide); the fused form of two or more types of different proteins (or peptides); or a newly designed polypeptide. Also as stated previously, cytochrome $P-450_{sca-2}$ is the preferred expression product, a suitable vector being pSCA1013-Δ(1013/428), said vector being isolatable from *Streptomyces lividans* SANK 62795 (FERM BP-5299).

It will be appreciated that the terms "expression product", "protein" and "polypeptide" are generally interchangeable, and are used in such a sense herein. In certain circumstances, the polypeptide translated from the original DNA is not the final product, but is an intermediate form of the final product, post-translational modifications being required to obtain the required product. In the case of $P-450_{sca-2}$, iron needs to be incorporated into a heme ring in the protein to generate the final expression product. Thus, while the terms "expression product", "protein" and "polypeptide" are used synonymously herein, the differences between the terms will be recognized by the person skilled in the art in the relevant context.

Outside of the actinomycetes, examples of suitable hosts for the promoters of the present invention include such prokaryotes as *Escherichia coli* and *Bacillus subtilis*.

In the event that non-actinomycete strains are used as hosts, or that the actinomycete strain selected is not appropriate to the type of vector, then it will be appreciated that the vector should comprise a replicon suitable to the strain in question, such as one originating in a species that is compatible with the host. A plasmid vector containing a replication origin and regulatory sequences appropriate to the host are required. In the event that the promoter of the present invention does not work in a particular host, and is not readily modified by a person skilled in the art so that it does work, even in the presence of other appropriate control sequences, then such a situation may be of limited use. For example, such a situation may be useful to multiply the promoter. It will be appreciated that, where such modifications and/or appropriate control sequences are readily available and/or recognized by those skilled in the art, then such situations are embodied by the present invention.

While expression vectors of the present invention need have no further features than those required for expression in a given host, it will be appreciated that built-in selection criteria can be useful. Such criteria include those whereby the plasmid confers on the host such properties as selectivity of expression and transformation, so that the phenotype is modified.

A suitable transformation method for use with an actinomycete comprises forming the actinomycete culture into spheroplasts using lysozyme. A buffer solution containing recombinant DNA vectors and polyethylene glycol is then added, in order to introduce the vector into the host cells, by using either of the methods of Thompson or Hopwood [c.f. Thompson, C. J., et al., (1982), J. Bacteriol., 151, 668–677 or Hopwood, D. A., et al., (1985), "Genetic Manipulation of Streptomyces: A Laboratory Manual", The John Innes Foundation, Norwich], for example. A thiostrepton-resistance gene is frequently used as a selective marker in the transformation plasmid [c.f. Hopwood, D. A., et al., (1987), "Methods in Enzymology" 153, 116, Academic Press, New York], but the present invention is not limited thereto.

If it is desired to transform *E. coli* in order to express a product under the control of a promoter of the present invention, then an appropriate general method is one wherein the relevant recombinant DNA vector is added to competent cells. The competent cells are generally prepared in the presence of salts such as calcium chloride, magnesium chloride and rubidium chloride [c.f. Hanahan, D., (1983), J. Mol. Biol. 166, 557–580]. An alternative method comprises electroporation, which involves the use of high-voltage pulses applied to a suspension comprising the host *E. coli* and the expression vector, thereby causing incorporation of the vector into the cells [c.f. Electroporation: Dower, W. J., et al., (1988), Nucleic Acid Res., 16, 6127 and Calvin, N. M., et al., (1988), J. Bacteriol., 170, 2796].

Suitable selective markers, i.e. those conferring a particular phenotype on the host, include such drug-resistance marker genes as those conferring resistance to ampicillin or tetracycline. However, many more will be apparent to those skilled in the art, and the present invention, as in all other cases of providing specific examples, is not limited thereby.

In the event that *B. subtilis* is intended as the host cell, then a suitable method is one wherein the host cells are made into protoplasts using lysozyme. A buffer solution containing recombinant DNA vectors and polyethylene glycol is then added to the protoplasts, followed by incorporation of the vector into the host cells by electroporation (supra) [c.f. Cheng, S., et al., (1979), Mol. Gen. Genet., 168, 111]. In a preferred embodiment, a drug-resistance marker, such as that for chloramphenicol resistance, is used as a selective marker for the transformed cell line, but it will be appreciated that many other selective markers may be used.

Regardless of the host, the desired transformant can be cultured using methods well known to those skilled in the art, with the desired polypeptide being produced by the culture either intracellularly or extracellularly, or both. Media that are used in the culture can be suitably selected from various types of media commonly used for the relevant host cells. In general, those culture conditions which are accepted as normal for the particular host can also be used for the expression of the desired polypeptide, subject to any modifications required by the properties of the polypeptide, for example.

For example, typical actinomycete nutrients include glucose, sucrose, starch, glycerol, starch syrup, molasses and soybean oil for use as the carbon source. As the nitrogen source, soybean powder, wheat germ, meat extract, peptone, corn steep liquor, dry yeast and ammonium sulfate are appropriate. In addition to the above, inorganic salts such as sodium chloride, potassium chloride, calcium carbonate or phosphate, and additives for assisting the growth of the micro-organism or promoting production of the desired polypeptide can also be suitably used in combination as necessary.

Again, culture techniques generally appropriate to the host in question are also applicable to the transformed micro-organisms, including such methods as liquid culturing and deep culturing, suitable for production on an industrial scale.

We prefer that culture conditions, unless otherwise generally contra-indicated, or specified herein, involve temperatures of between 20° and 37° C., preferably between 26° and 28° C.

The expression product under the control of a promoter of the present invention is generally produced intracellularly or extracellularly, and occasionally both. The product can be isolated, purified and recovered by various procedures, such as are well known to those skilled in the art, particularly those procedures relying upon the physical or chemical properties of the polypeptide. In the case where the polypeptide is expressed externally, the polypeptide can be isolated, purified and recovered from the resulting supernatant by centrifuging the culture medium, for example, to remove cells.

In order to isolate and purify a polypeptide which has accumulated inside the cells, then the cells are first suspended in a solution containing a protease inhibitor and then homogenized using a means, such as one commonly known to those skilled in the art such as, for example, an ultrasonic homogenizer.

Although it is not generally necessary for the elucidation of the present invention, it will be appreciated that examples of specific methods for the isolation, purification and collection of the desired polypeptides include such techniques as protein precipitation, ultrafiltration, molecular sieve chromatography (gel filtration), adsorption chromatography, ion exchange chromatography, affinity chromatography, the various appropriate types of liquid chromatography, including high-performance liquid chromatography (HPLC), dialysis and combinations thereof.

In any event, it will be appreciated that the desired polypeptide can easily be produced on an industrial scale, both in high yield and in high purity, using the present invention.

It will also be appreciated that it is possible to assay the activity of the polypeptide produced by transformed host cells of the present invention using an unpurified, or partially purified, preparation sample. $P\text{-}450_{sca\text{-}2}$ can be obtained from *Streptomyces lividans* in a manner as described above, and used directly in the production of pravastatin sodium, for example. The necessary electron transport system is present in the *S. lividans* cells, so that it is relatively straightforward to obtain a transformed host micro-organism that catalyzes hydroxylation at the 6-position of ML-236B sodium.

In the present embodiment, the promoter is typically used to help express the cytochrome, but this can then be used in the production of, for example, pravastatin sodium. Any pravastatin sodium produced by the process can then be recovered by the method of Serizawa, et al. [c.f. Serizawa, N., et al., (1983), J. Antibiotics, 36, 608]. *Streptomyces lividans* SANK 62795 (FERM BP-5299) may be used in such a manner.

The present invention will now be further described with reference to the following Examples, the Examples being illustrative of, but not binding on, the present invention. Any methods, preparations, solutions and such like which are not specifically defined may be found in "Molecular Cloning—A Laboratory Handbook" (supra) which is hereby incorporated in its entirety by this reference. All solutions are aqueous, unless otherwise specified.

In the following Examples, we demonstrate that it was possible to produce a desired polypeptide in a host micro-organism using a promoter of the present invention.

EXAMPLE 1

Isolation of the P-450$_{sca-2}$ Promoter and Construction of a Plasmid Vector for the Expression of Cytochrome P-450$_{sca-2}$ (1-1) Construction of Plasmids pSCA101 and pSCA108

Figure 4:
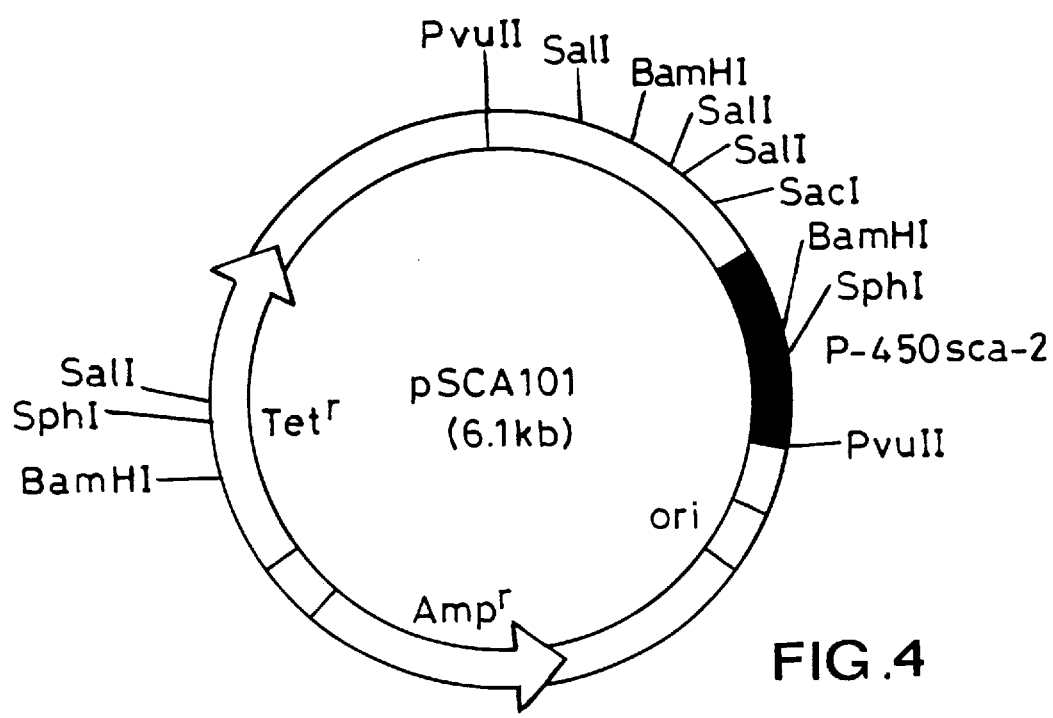
FIG. 4 is a restriction map of a plasmid, pSCA101, containing a part of the P-450$_{sca-2}$ gene together with the 1 kbp 5' promoter.

Plasmids pSCA101 and pSCA108 were constructed by cloning different fragments of the region containing the P-450$_{sca-2}$ gene and promoter, these fragments being derived from the genomic DNA of *Streptomyces carbophilus* in accordance with the method described by Watanabe and co-workers [c.f. Watanabe, I., et al., (1995), Gene, 163, 81–85 and Japanese Patent Kokai No. Hei 6-70780]. FIG. 4 is a map of the plasmid pSCA101. This plasmid was constructed by the ligation of a 1.7 kbp PvuII fragment, derived from *Streptomyces carbophilus* genomic DNA, into the PvuII site of pBR322 (obtained from Takara Shuzo Ltd., Japan). This 1.7 kbp DNA fragment contains the whole of the 5' promoter of the P-450$_{sca-2}$ gene and DNA encoding the 5' end of the gene. The plasmid pSCA108 was constructed by the ligation of a 2.0 kbp SacI fragment, derived from *Streptomyces carbophilus* genomic DNA, into the SacI site of pUC18 (obtained from Takara Shuzo Ltd., Japan). This 2.0 kbp fragment contains the entire coding region of cytochrome P-450$_{sca-2}$ gene.

The details of the above techniques are as follows.

(1-2) Construction of pSCA106

Using 100 units of PvuII, 10 μg of pSCA101 DNA were digested at 37° C. for 3 hours. The digestion was carried out in the restriction buffer supplied with the enzyme (Takara Shuzo). Specifically, the buffer used was H buffer, as supplied by Takara Shuzo, Japan. In the following Examples, as here, where restriction enzymes are used, but the source and/or the buffer are not specified, then the enzyme is supplied by Takara Shuzo and is used in accordance with the supplier's recommendations, and the buffer is H, K or L buffer, as appropriate, also as supplied by Takara Shuzo.

The products of the digestion reaction were separated by agarose gel electrophoresis on a 1% w/v agarose gel, the agarose gel being placed in a submarine-type electrophoresis tank containing an aqueous solution of 90 mM Tris-HCl buffer, 90 mM boric acid and 2.5 mM EDTA (pH 8.3), and which was run at 100 V for 3 hours.

Following electrophoresis, the gel was shaken in an aqueous solution of ethidium bromide (0.5 μg/ml) for 20 minutes, to stain the DNA. An agarose slice containing the relevant 1.7 kbp fragment was excised from the gel, using a razor blade. Long wave UV irradiation allowed the stained DNA fragments to be identified. The excised 1.7 kbp fragment was transferred to a dialysis tube (permeation limit: 12000–14000 Da, Gibco) which was then sealed. This sealed tube was next placed in a submarine-type electrophoresis tank containing an aqueous solution of 90 mM Tris-HCl buffer (pH 8.3), 90 mM boric acid and 2.5 mM ethylenediamine tetraacetic acid (EDTA).

The DNA fragment was then eluted from the agarose gel slice using a current of 100 V for 2 hours. The resulting solution in the dialysis tube was next treated with a 50:50 v/v mix of phenol and chloroform to bring any contaminating proteins into the resulting organic phase. This method is routine, and well known to those skilled in the art. The DNA was subsequently recovered from the aqueous phase by the standard technique of ethanol precipitation, and dried under reduced pressure [c.f. "Molecular Cloning—A Laboratory Manual", supra]. This method of recovery of DNA from agarose, as described above, is referred to herein as "excision".

Using 10 units of the restriction enzyme SmaI, 10 μg of pUC119 DNA (Takara Shuzo) were digested at 25° C. for 3 hours. The digested DNA was treated with a 50:50 v/v phenol-chloroform mix (referred to hereinafter simply as phenol-chloroform) and recovered by ethanol precipitation in a manner similar to that described above, and the recovered DNA was then dried under reduced pressure.

The cut ends of the linearized plasmid were dephosphorylated using 4 units of alkaline phosphatase (Toyobo). The dephosphorylation reaction was carried out at 37° C. for 30 minutes in 200 μl of TE buffer (10 mM Tris-HCl, 1 mM EDTA, pH 8.0, made up in distilled water). After this time, the solution was treated with phenol-chloroform and the dephosphorylated DNA was recovered from the aqueous phase by ethanol precipitation and dried under reduced pressure.

A 50 ng amount of the 1.7 kbp PvuII fragment obtained above were added to 100 ng of the dephosphorylated, SmaI pUC119 DNA in 50 μl of ligase buffer (6.6 mM magnesium chloride, 10 mM dithiothreitol, 0.1 mM ATP and 66 mM Tris-HCl, pH 7.6, made up in distilled water) containing 1800 units of T4 DNA ligase (Takara Shuzo), and the ligation reaction was carried out for 2 hours. Competent *E. coli* strain HB101 cells were transformed with a portion of the ligation reaction solution, in accordance with the method of Hanahan [c.f. Hanahan, D., (1980), J. Mol. Biol., 166, 557–580]. The resulting transformed cells were grown up in L medium (10 g/liter of tryptone, 5 g/liter of yeast extract and 5 g/liter of sodium chloride, made up in distilled water), containing 100 μg/ml of ampicillin.

Cells grown up in L medium were then plated onto solid L medium at 37° C., and ampicillin-resistant colonies were selected. Colonies selected by this technique were further propagated on solid L medium, and plasmid DNA was prepared from a selected number of transformants. The plasmid DNA from each transformant was digested with the appropriate restriction enzymes, and the resulting DNA was analyzed by agarose gel electrophoresis to confirm identify a transformant containing the expected plasmid. The plasmid constructed in this way was named pSCA106.

(1-3) Construction of pSCA111

The plasmid pSCA111 contains the 5' promoter region of the P-450$_{sca-2}$ gene, from plasmid pSCA106, ligated to the P-450$_{sca-2}$ structural gene, derived from pSCA108. The protocol was as follows.

10 μg of the pSCA108 DNA obtained above were digested with 100 units of SacI at 37° C. for 5 hours in the buffer supplied with the kit (Takara Shuzo). The resulting digestion products were separated by electrophoresis on a 1% w/v agarose gel, and a 2.0 kbp SacI DNA fragment was excised from the gel.

At the same time, 10 μg of pSCA106 DNA, as obtained above, were digested at 37° C. for 3 hours with 100 units of SacI in the buffer supplied with the kit. The digestion products were separated by electrophoresis on a 1% w/v agarose gel, and a 4 kbp SacI fragment was excised from the gel.

The termini of the 4 kbp SacI fragment, thus obtained, were dephosphorylated in a similar manner to that described in section (1-2). After dephosphorylation, the solution was treated with phenol-chloroform and the DNA was recovered from the aqueous phase by ethanol precipitation, and dried under reduced pressure.

100 ng of the resulting dephosphorylated 4 kbp SacI DNA fragment and 50 ng of the 2.0 kbp SacI DNA fragment obtained in the first portion of this section, and which contains the structural gene of P-450$_{sca-2}$, were mixed in ligase buffer containing 1800 units of T4 DNA ligase to a final volume of 50 μl, and the ligation reaction was carried out for 2 hours at 16° C. Competent *E. coli* strain HB101 cells were transformed with a portion of the ligation reaction, in a manner similar to that described in section (1-2) above, and pSCA111 was obtained.

(1-4) Construction of pSCA212

From the pSCA111 DNA obtained in 1-3, 10 μg of DNA were digested with 100 units each of XbaI and PstI for 3 hours at 37° C. The resulting digested DNA was treated with phenol-chloroform and the DNA was recovered from the aqueous phase by ethanol precipitation and dried under reduced pressure.

Next, the region upstream of the P-450$_{sca-2}$ gene contained in pSCA111 was deleted in a 5'→3' direction as described by Henikoff [c.f. Henikoff, S., (1984), Gene, 28, 351–359]. Two hundred units of exonuclease III (Takara Shuzo) were added to 10 μg of the dried pSCA111DNA in 100 μl of exonuclease buffer (50 mM Tris-HCl, 5 mM magnesium chloride, 10 mM 2-mercaptoethanol, pH 8.0, made up in distilled water), and the reaction was allowed to proceed for 5 minutes at 37° C. After this time, the reaction was stopped by heating at 65° C. for 5 minutes and then the reaction solution was treated with phenol-chloroform. DNA was then recovered from the aqueous phase by ethanol precipitation and dried under reduced pressure.

The resulting dried DNA was treated with 50 units of mung bean nuclease (Takara Shuzo) in 40 μl of 30 mM acetate buffer (pH 5.0), containing 100 mM sodium chloride, 1 mM zinc acetate and 5% (v/v) glycerol for 30 minutes at 37° C. Once again, the DNA was treated with phenol-chloroform, recovered from the aqueous phase by ethanol precipitation, and dried under reduced pressure.

The precipitated DNA was treated with 5 units of T4 DNA polymerase (Takara Shuzo) in 10 μl of T4 DNA polymerase buffer [33 mM Tris-HCl, 66 mM potassium acetate, 10 mM magnesium acetate, 0.5 mM dithiothreitol, 0.1 mg/ml bovine serum albumin (Takara Shuzo), pH 7.9, made up in water] at 37° C. for 5 minutes. The thus treated DNA was then treated with phenol-chloroform, extracted by ethanol precipitation, and dried under reduced pressure.

The combination of treatment with mung bean nuclease and T4 DNA polymerase ensured that the DNA fragment had no sticky 5' or 3' ends.

The DNA was then treated with 10 units of alkaline phosphatase in a final volume of 400 μl of alkaline phosphatase buffer (50 mM Tris-HCl, 1 mM magnesium chloride, pH 9.0, made up in distilled water) for 30 minutes at 37° C. The reaction product was subsequently treated with phenol-chloroform, extracted by ethanol precipitation, and dried under reduced pressure.

The resulting DNA was mixed with 100 ng of a phosphorylated XbaI linker (Takara Shuzo) in ligase buffer containing 1800 units of T4 DNA ligase to a final volume of 50 μl, and the ligation reaction was allowed to proceed for 2 hours at 16° C. Competent *E. coli* strain HB101 cells were transformed with a portion of the ligation reaction, in a manner similar to that described in section (1-2), and pSCA212 was obtained.

(1-5) Construction of plasmid pSCA301

Ten μg of the multi-copy plasmid pIJ702 [c.f. Katz, E., et al., (1983), J. Gen. Microbiol., 129, 2703–2714] were digested at 37° C. for 3 hours with 100 units of SacI and 100 units of SphI in H buffer. The digestion products were electrophoresed on a 1% w/v agarose gel, and the DNA fragment corresponding to the 5.4 kbp band was excised from the gel.

As part of the cloning procedure, it was necessary to prepare a double-stranded oligonucleotide having internal HindIII and EcoRI cleavage sites, as well as DNA ends suitable for ligation into SacI and SphI sites. Such a double stranded oligonucleotide was constructed by annealing the two single stranded oligonucleotides described below. Both oligonucleotides were synthesized by the phosphoramidite method, using a DNA synthesizer (Model 380, Applied Biosystems) [c.f. Beaucage, S. L., et al., (1981), Tetrahedron Letters, 22, 1859–1862]. The sequences are:

SEQ ID NO. 2 5'-GATCTAAGCTTGAATTCGCATG-3'
SEQ ID NO. 3 5'-CGAATTCAAGCTTA-3'

Fourteen μmol of each oligonucleotide were mixed together in TE buffer to a final volume of 400 μl. The mixture was heated to 100° C. for 5 minutes, and then gradually cooled to 25° C. A double-strand oligonucleotide was formed between the two complementary single-stranded oligonucleotides.

100 ng of the thus obtained double-stranded oligonucleotide were mixed with 1 μg of the 5.4 kbp fragment of pIJ702 which had been digested with SacI and SphI in ligase buffer containing 1800 units of T4 DNA ligase to a final volume of 100 μl, and the ligation reaction was allowed to proceed for 2 hours at 16° C. A portion of the ligation reaction was transformed into spheroplasts prepared from *Streptomyces lividans* strain TK21. The resulting transformants were cultured in the presence of thiostrepton to select cells containing the plasmid. The procedure using *Streptomyces lividans* strain TK21 is described in method [1] below. Plasmid DNA was then isolated from the thiostrepton-resistant transformants in accordance with method [2] below.

Method [1]

Transformation of *Streptomyces lividans* strain TK21

Transformation of *Streptomyces lividans* TK21 was performed according to the method of Thompson [c.f. Thompson, C. J., et al., (1982), J. Bacteriol., 151, 668–677]. Details of the solutions used are given at the end of this protocol.

A streak of *Streptomyces lividans* strain TK21 [c.f. Hopwood, D. A., et al., (1983), J. Gen. Microbiol., 129, 2257–2269] was inoculated into 20 ml of liquid GPY medium and cultured for 3 days at 28° C., with shaking, at 120 rpm. After this time, the cells in this liquid pre-culture medium were resuspended using a Teflon® homogenizer and 5 ml of the liquid medium were diluted into 110 ml of S-GGCY medium, and the cells were then grown up for a further 24 hours in a Sakaguchi flask at 28° C., with shaking, at 120 rpm. After this time, the cells in the culture medium were harvested by centrifugation (10 minutes, 4° C., 1,600× g). The resulting pellet was washed with P buffer and centrifuged again (10 minutes, 4° C., 1,600×g) to obtain a pellet and the washing step was performed twice more.

One gram of the washed pellet of cells was resuspended in 10 ml of P buffer and then an equal volume of P buffer, containing 20 mg/ml of lysozyme, was added to the cell suspension, and the whole was cultured with gentle shaking for 1.5 hours at 30° C. and 120 rpm. This results in the formation of *Streptomyces lividans* TK21 spheroplasts.

The suspension of spheroplasts was then filtered twice, each time through 8 pieces of gauze, and then centrifuged for 10 minutes at 4° C. and 1,600×g to obtain a pellet. The pelleted spheroplasts were then washed twice with P buffer as above, and harvested by centrifugation for 10 minutes at 4° C. and 1,600×g. The pellet was resuspended in 0.8 ml of P buffer and allowed to stand on ice. 20 μl of the ligation reaction were then added to 100 μl of the spheroplast suspension, and the suspension was allowed to stand on ice for a further 2 minutes, after which time 500 μl of P buffer containing 20% (w/v) polyethylene glycol 1540 was added to the suspension. The suspension was then left on ice for a further 2 minutes, after which time 5 ml of P buffer were added. One hundred µl of this suspension were then gently layered onto a plate of 10 ml of regeneration medium containing 2% (w/v) bactoagar, and the cells were grown up on this solid medium at 28° C. for approximately 20 hours. Five ml of liquid regeneration medium, containing 0.7% (w/v) bactoagar and 75 µg/ml thiostrepton, were warmed to 45° C., and poured onto the agar plate. The plate was then incubated at 28° C., and a thiostrepton-resistant strain was isolated after 3 to 5 days.

The compositions of the media and buffers used in the above-mentioned transformation procedure are as shown below. Distilled water was used as the solvent in all cases.

| a) GPY Medium | |
|---|---|
| Glucose | 20 g/liter (w/v) |
| Polypeptone | 10 g/liter (w/v) |
| Yeast extract | 1 g/liter (w/v) |
| | (pH 7.0–7.2) |
| b) S-GGCY Medium | |
| Solution A: | |
| Saccharose | 340 g/liter (w/v) |
| Glycerol | 4 g/liter (w/v) |
| Glycine | 1 g/liter (w/v) |
| Casamino acid | 4 g/liter (w/v) |
| Yeast extract | 1 g/liter (w/v) |
| Magnesium sulfate-7 hydrate | 1 g/liter (w/v) |
| Calcium chloride-2 hydrate | 0.1 g/liter (w/v) |
| Trace metal salt solution[e] | 4 ml/liter (v/v) |

Solution B

Potassium dihydrogenphosphate 20 g/liter (w/v)

Dipotassium hydrogenphosphate-12 hydrate 80 g/liter (w/v)

Solutions A and B were separately sterilized and 100 ml of A was mixed with 10 ml of B.

| c) P Buffer | |
|---|---|
| Saccharose | 102 g/liter (w/v) |
| Potassium sulfate | 0.248 g/liter (w/v) |
| Magnesium chloride-6 hydrate | 2.00 g/liter (w/v) |
| Trace metal salt solution[e] | 1.98 ml/liter (v/v) |
| Potassium dihydrogenphosphate | 49.5 g/liter (w/v) |
| Calcium chloride-1 hydrate | 3.64 g/liter (w/v) |
| TES (pH 7.2) | 5.67 g/liter (w/v) |
| d) Regeneration Medium | |
| Saccharose | 100 g/liter (w/v) |
| Glucose | 9.69 g/liter (w/v) |
| Casamino acid | 96.9 mg/liter (w/v) |
| Yeast extract | 1.94 g/liter (w/v) |
| Malt extract | 4.84 g/liter (w/v) |
| Potassium sulfate | 243 mg/liter (w/v) |
| Magnesium chloride-6 hydrate | 9.84 g/liter (w/v) |
| Potassium dihydrogenphosphate | 48.4 mg/liter (w/v) |
| Calcium chloride-2 hydrate | 2.85 g/liter (w/v) |
| TES (pH 7.2) | 5.56 g/liter (w/v) |
| Trace metal salt solution[e] | 1.94 ml/liter (v/v) |
| Sodium hydroxide | 0.00484 N |
| L-proline | 2.91 g/liter (w/v) |
| DL-norleucine | 48.4 mg/liter (w/v) |
| L-tyrosine | 0.969 g/liter (w/v) |
| e) Trace Metal Salt Solution | |
| Zinc chloride | 40 mg/liter (w/v) |
| Iron (II) chloride-6 hydrate | 200 mg/liter (w/v) |

| -continued | |
|---|---|
| Copper (II) chloride-2 hydrate | 10 mg/liter (w/v) |
| Manganese (II) chloride-4 hydrate | 10 mg/liter (w/v) |
| Sodium borate-10 hydrate | 10 mg/liter (w/v) |
| Ammonium molybdate-4 hydrate | 10 mg/liter (w/v) |

Method [2]

Preparation of plasmid DNA from Actinomyces

The thiostrepton-resistant strain obtained in method [1] above was grown for 3 days at 28° C. and 200 rpm in a shaking incubator (Tokyo Dennetsu Keiso Co. Ltd., Japan) in 100 ml of GPY medium, containing 25 µg/ml of thiostrepton. The cells in the culture medium were then pelleted by centrifugation at 4,000×g and 4° C. for 10 minutes. The resulting pellet was resuspended in 4 ml of 25 mM Tris-HCl buffer (pH 8.0) containing 10 mg/ml of lysozyme (Sigma), 50 mM glucose and 10 mM EDTA and incubated at 30° C. for 1 hour. After this time, the cell suspension was mixed with 8 ml of 1% (w/v) sodium dodecylsulfate solution containing 0.2M sodium hydroxide. The resulting mixture was stirred and allowed to stand for 10 minutes on ice. After this time, 6 ml of an aqueous solution of 3M sodium acetate (pH 4.8) were added to the mixture which was mixed and then centrifuged at 11,000×g, at 4° C. for 15 minutes.

The whole of the resulting supernatant was applied to a Qiagen chips 500 column (Funakoshi), which had previously been equilibrated with 10 ml of adsorption buffer [50 mM 3-(N-morpholino)propane-sulfonic acid ("MOPS"), 750 mM sodium chloride, 15% (v/v) ethanol, 0.15% (v/v) Triton X-100, (pH 7.0), made up in water]. The column was then washed with 30 ml of wash buffer [50 mM MOPS, 1M sodium chloride, 15% (v/v) ethanol, pH 7.0, made up in water], and then the plasmid DNA was eluted from the column using 15 ml of elution buffer [50 mM Tris-HCl, 1.25M sodium chloride, 15% (v/v) ethanol, pH 8.5, made up in water].

10.5 ml of isopropanol were added to the resulting eluate, and this mixture was centrifuged for 15 minutes (11,000×g, 4° C.) to precipitate the DNA. The precipitated DNA was resuspended in 400 Al of TE buffer, to which was subsequently added 5 µl of 2 mg/ml ribonuclease A (Sigma), to remove any contaminating RNA, the reaction being allowed to proceed for 30 minutes at 37° C. After this time, the DNA was treated with phenol-chloroform and precipitated by treating the aqueous layer with ethanol. The precipitated plasmid DNA was dried under reduced pressure.

(1-6) Construction of pSCA1013-Δ(1013/428)

Ten µg of pSCA301 DNA obtained in 1-5 above were digested with 100 units of EcoRI and 100 units of HindIII for 3 hours at 37° C. in H buffer. The resulting digestion product was treated with phenol-chloroform, and DNA was extracted from the aqueous phase by ethanol precipitation. The precipitated DNA was dried under reduced pressure.

In parallel, 10 µg of pSCA212 were digested with 100 units of EcoRI and 100 units of HindIII at 37° C. for 3 hours in H buffer. The digestion products were electrophoresed on a 1% w/v agarose gel, and the 2.2 kbp DNA fragment encoding the cytochrome P-4505$_{sca-2}$ gene was excised from the gel.

200 ng of the thus obtained 2.2 kbp pSCA212 DNA fragment were added to 100 ng of the EcoRI-HindIII pSCA301 DNA fragment in 100 µl of ligase buffer containing 1800 units of T4 DNA ligase, and the ligation reaction was carried out at 16° C. for 2 hours. After this time, the DNA from the ligase reaction was transformed into Streptomyces lividans as described in method [1] above, and the thiostrepton-resistant *Streptomyces lividans* strain obtained by this method was named SANK 62795. Plasmid DNA was obtained from this strain by method [2] above, and this plasmid was named pSCA1013-Δ(1013/428).

Figure 3:
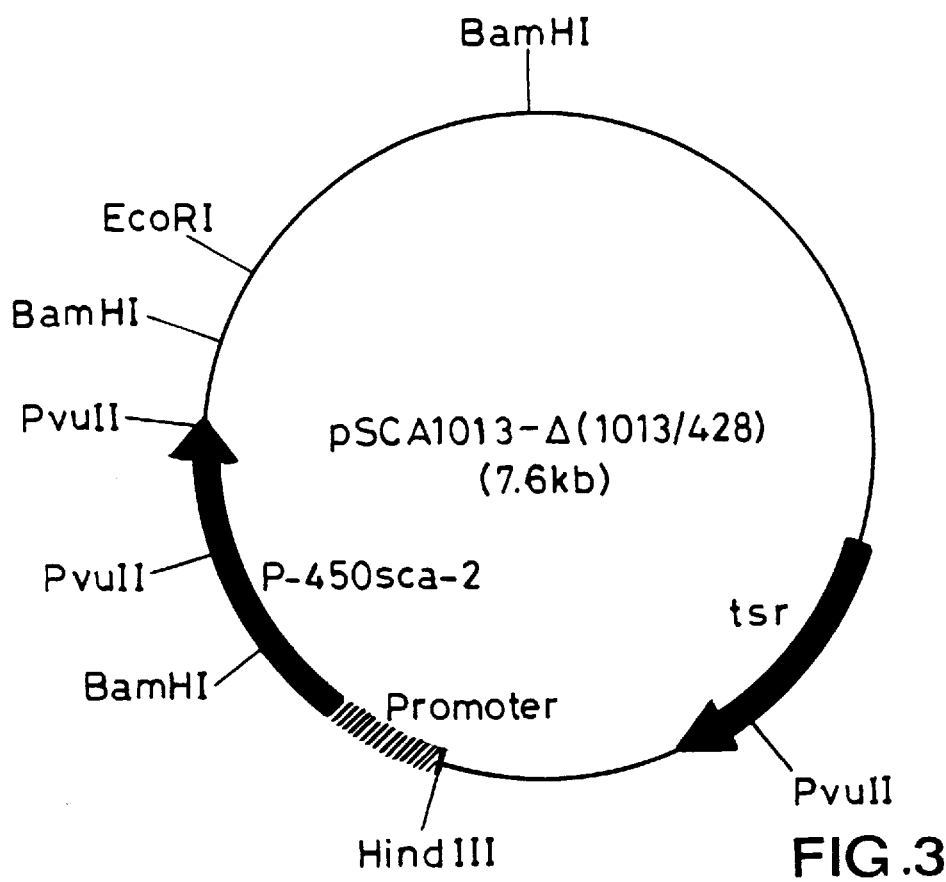
FIG. 3 is a restriction map of the plasmid, pSCA1013-Δ (1013/428), obtained in FIG. 1.

The process of this section is depicted in FIG. 1, and the map of the resulting plasmid is shown in FIG. 3. The pSCA1013-Δ(1013/428) plasmid obtained is capable of replicating in Actinomyces spp. It contains approximately 0.4 kbp of DNA derived from the 5' promoter of the cytochrome P-450$_{sca-2}$ gene, and includes all of the P-450$_{sca-2}$ coding sequence.

(1-7) Construction of pSCA205

Ten μg of pSCA111, as obtained in Example 1–3, were treated with HindIII at 37° C. for 5 hours in H buffer, after which time the reaction solution was treated with phenol-chloroform and precipitated with ethanol and the precipitated DNA dried under reduced pressure. The HindIII termini of pSCA111 were blunted using a DNA blunting kit (Takara Shuzo). The blunted fraction was treated with phenol-chloroform and the DNA precipitated with ethanol and dried under reduced pressure.

The resulting DNA was dissolved in 200 μl of TE buffer, and 4 units of alkaline phosphatase (Toyobo) were added to the solution. This solution was then incubated at 37° C. for 30 minutes in order to dephosphorylate the blunted ends. The dephosphorylated fragment was then treated with phenol-chloroform, recovered from the aqueous phase by ethanol precipitation, and dried under reduced pressure.

Figure 5:
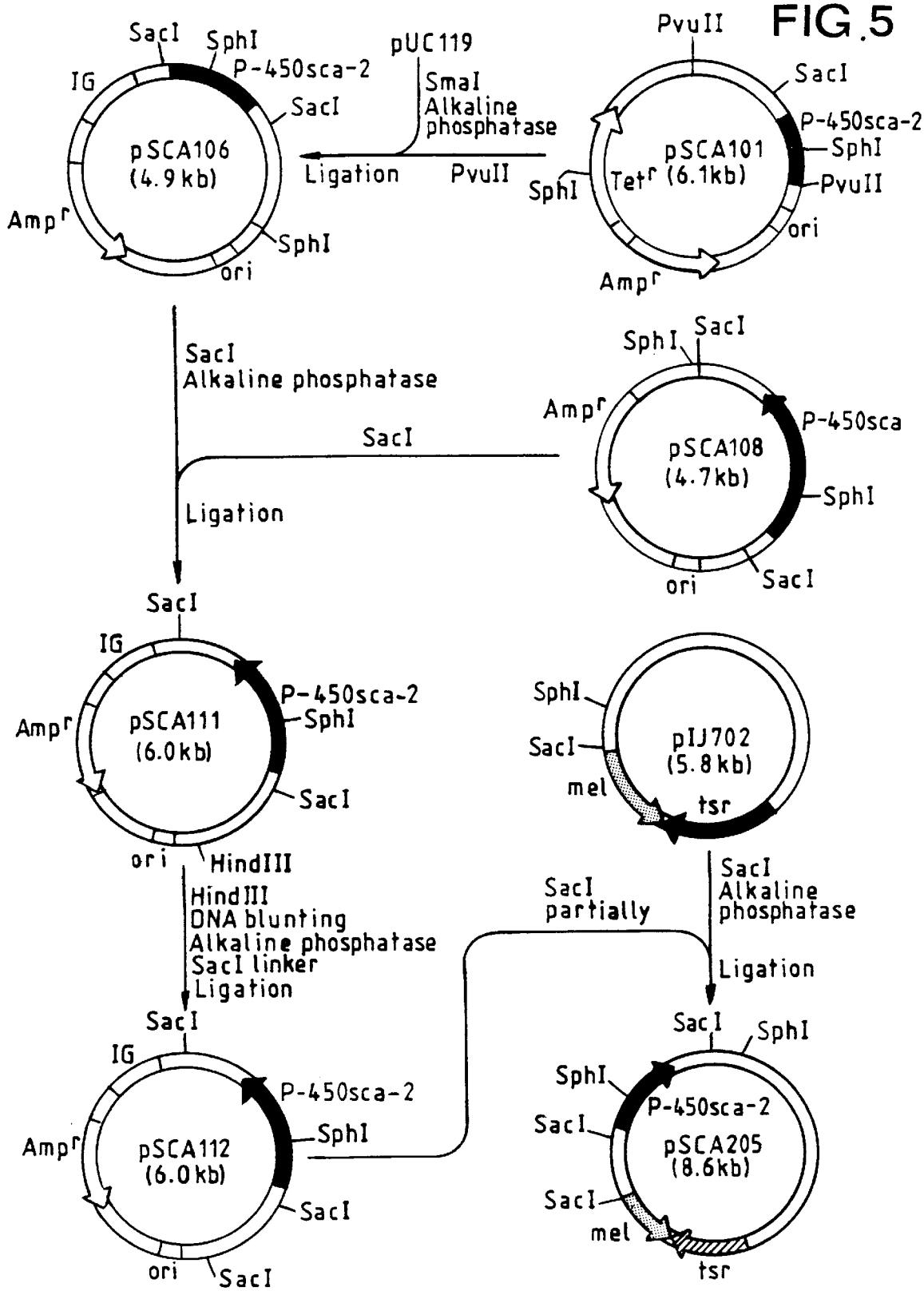
FIG. 5 is a plan for the construction of a plasmid, pSCA205, containing the 1 kbp 5' promoter and the P-450$_{sca-2}$ ORF.

16.5 ng of SacI linker was then added to 100 ng of the dephosphorylated and blunted pSCA111, and the fragment was circularized using a DNA ligation kit (Takara Shuzo) to form the plasmid pSCA112, in which the HindIII site of pSCA111 is substituted by a SacI site (see FIG. 5).

In order to obtain a 2.8 kbp SacI fragment from pSCA112 containing the structural P-450$_{sca-2}$ gene and its promoter, pSCA112 was partially digested with SacI as follows. 22.1 μg of pSCA112 was treated with 1250 units of SacI at 37° C. for 22 hours in L buffer. The resulting fragments were electrophoresed on a 1% w/v agarose gel and a 2.8 kbp fragment was excised. This fragment was transferred into a dialysis tube and eluted against a 1×TBE buffer at 150 V for 1.5 hours to obtain the 2.8 kbp SacI fragment. The solution containing the SacI fragment was treated with phenol-chloroform and the DNA precipitated with ethanol and dried under reduced pressure.

The whole of the resulting DNA was dissolved in TE buffer containing 1 g/ml of cesium chloride followed by the addition of ethidium bromide up to 0.1 mg/ml. The resulting solution was centrifuged at 120,000 rpm (650,000×g) at 15° C. for 2 hours to isolate the 2.8 kbp of SacI fragment. The pellet was then extracted three times with isopropanol saturated with sodium chloride and containing 50 mM Tris-HCl buffer (pH 8.0), in order to remove ethidium bromide. The wash was then followed by overnight dialysis in TE buffer at 4° C. The resulting fraction was precipitated with ethanol, then washed with an aqueous solution of 70% v/v ethanol and dried under reduced pressure to yield 76 μg of the partially purified SacI fragment (2.8 kbp).

This partially purified SacI fragment was contaminated with a 3.2 kbp DNA fragment originally derived from pUC119. In order to remove this fragment, 75 μg of the partially purified SacI fragment (2.8 kbp) was treated with 205 units of PvuI at 37° C. for 12 hours in K buffer. The reaction product was then electrophoresed on a 1% w/v agarose gel to obtain the 2.8 kbp SacI fragment. The excised fragment of gel was dialyzed as before but, this time, for only 1 hour, to elute the DNA fragment. The dialyzed solution was treated with phenol-chloroform and the DNA precipitated and dried under reduced pressure.

The dried DNA was then dissolved in 2 ml TE buffer containing 1 g/ml of cesium chloride, followed by the addition of ethidium bromide up to 0.1 mg/ml. The resulting solution was centrifuged at 120,000 rpm (650,000×g) at 15° C. for 2 hours to isolate the 2.8 kbp SacI fragment. The isolate was then extracted three times with isopropanol saturated with sodium chloride and containing 50 mM Tris-HCl buffer (pH 8.0), in order to remove ethidium bromide. After this washing, the fragment was dialyzed in TE buffer at 4° C. overnight. This dialyzed DNA was then precipitated with ethanol and washed with an aqueous preparation of 70% v/v ethanol and dried under reduced pressure. The dried DNA was dissolved in 20 μl of TE buffer. The final yield was 9.8 μg of the SacI fragment (2.8 kbp) containing the structural P-450$_{sca-2}$ gene and its promoter.

In parallel, 200 μg of pIJ702 was treated with 300 units of SacI at 37° C. for 20 hours in L buffer. The solution was treated with phenol-chloroform and the aqueous layer was treated with ethanol to precipitate the DNA and the precipitated DNA was dried under reduced pressure. The dried DNA was dissolved in 800 μl of TE buffer and then 80 units of alkaline phosphatase were added to the reaction medium and kept at 37° C. for 30 minutes. After this time, the solution was again treated with phenol-chloroform and the aqueous layer was treated with ethanol to precipitate the DNA and the precipitated DNA was dried under reduced pressure. The dried DNA was dissolved in TE buffer containing 1 g/ml of cesium chloride, followed by addition of ethidium bromide up to 0.1 mg/ml. The resulting solution was centrifuged at 120,000 rpm (650,000×g) at 15° C. for 2 hours to isolate the SacI-treated pIJ702.

The resulting pellet was extracted three times with isopropanol saturated with sodium chloride and containing 50 mM Tris-HCl buffer (pH 8.0), in order to remove ethidium bromide. The fragment was then dialyzed in TE buffer at 4° C. overnight. This dialyzed DNA was then precipitated with ethanol and washed with an aqueous preparation of 70% v/v ethanol and dried under reduced pressure. The above process yielded 37 μg of SacI and alkaline phosphatase treated pIJ702.

2.4 μg of the 28 kbp SacI fragment prepared from pSCA112 was added to the SacI and alkaline phosphatase treated pIJ702 in TE buffer. The two fragments were ligated with a DNA ligation kit (Takara Shuzo). *Streptomyces lividans* TK 21 was transformed with the resulting plasmid, and the plasmid was purified from the transformant by the method of Hopwood (Hopwood et al., "Genetic Manipulation of Streptomyces—A Laboratory Manual": John Innes Institute, Norwich, 1985). This plasmid was named pSCA205.

EXAMPLE 2

Nucleotide Sequencing

Plasmid DNA as obtained in Example 1 was prepared for sequencing by alkaline denaturation using the method of Zhang [c.f. Zhang, H. et al., (1988), Nucleic Acids Res., 16, 1220]. Denaturation was performed by incubating 5 μg of plasmid DNA for 5 minutes at 37° C. in 20 μl of 10 mM Tris-HCl buffer (pH 8.0) containing 0.2 mM EDTA and 0.2M sodium hydroxide. DNA was recovered from this solution by ethanol precipitation. The precipitated DNA was washed with 70% (v/v) ethanol, and dried under reduced pressure. The resulting DNA was used as the template for nucleotide sequencing.

DNA sequencing was performed using the 7-deazasequenase kit, version 2.0 (Toyobo). The results indicate that the 5' region of the cytochrome P-450$_{sca-2}$ gene present in plasmid pSCA1013-Δ(1013/428) is 428 bp long. This sequence is reproduced as SEQ ID NO. 1, nucleotide nos. 1–428.

EXAMPLE 3

The Production and Measurement of Pravastatin Sodium

Single colonies of each of the *Streptomyces lividans* strains SANK 62795, *S. lividans* TK21/pSCA205 and TK21 were inoculated from solid media into separate 500 ml Erlenmeyer flasks, each containing 100 ml of yeast medium [2% (w/v) glucose, 1% (w/v) peptone, 0.1% (w/v) yeast extract (Difco), pH 7.0, made up in distilled water] containing 20 μg/ml of thiostrepton. The cultures were grown up for 3 days with shaking, at 28° C. and 200 rpm. Five ml of each culture medium were inoculated into separate lots of 100 ml of yeast medium containing 20 μg/ml of thiostrepton and each was further cultured for 24 hours at 28° C. and 200 rpm. After this time, ML-236B sodium was added to a final concentration of 500 μg/ml [c.f. Endo, A., et al., (1976), J. Antibiotics, 29, 1346 and Serizawa, N., et al., (1983), J. Antibiotics, Vol XXXVI, No 7, 887–891] and culturing with shaking at 28° C. and 200 rpm was continued for a further hour. After this time, a portion of each of the liquid cultures was removed and was used to measure the production of pravastatin sodium. Each sample was analyzed by high-performance liquid chromatography, under the operating conditions:

Column: Radial pack cartridge C18 (Waters)

Solvent: 0.1% w/v phosphate buffer containing 30% v/v acetonitrile and 0.1% v/v triethylamine, pH 3.2

Flow rate: 1 ml/min

Detection wavelength: 237 nm

Pravastatin sodium retention time: 11.9 minutes

Chromatography was also performed on a known amount of pravastatin sodium, under conditions identical to those described above, for use as a standard reference [c.f. Serizawa, N., et al., (1983), J. Antibiotics, 36, 608]. The amount of pravastatin sodium produced from the different strains of *S. lividans* was calculated by comparing the area of the pravastatin peak of the detection chart with the area of the pravastatin peak of a known amount of pravastatin standard.

*Streptomyces lividans* strain SANK 62795 produced 51 μg/ml of pravastatin sodium, *S. lividans* TK21/pSCA205 produced 11 μg/ml of pravastatin sodium while *Streptomyces lividans* strain TK21 did not produce any detectable pravastatin sodium. This clearly demonstrates the advantage of the promoters of the present invention.

EXAMPLE 4

Construction of Plasmids pSCA1013-Δ(1013/320), pSCA1013-Δ(1013/158), pSCA1013-Δ(1013/101) and pSCA1013-Δ(1013/74)

In order to better characterize the promoter region of the P-450$_{sca-2}$ gene, a number of plasmids were constructed which contained different fragments of the 5' promoter region attached to the P-450$_{sca-2}$ structural gene. Hereafter, the term "P-450$_{sca-2}$" will be used to refer to the structural gene encoding the intact amino acid sequence of P-450$_{sca-2}$.

The plasmids of this Example, namely pSCA1013-Δ (1013/320), pSCA1013-Δ(1013/158), pSCA1013-Δ(1013/101) and pSCA1013-Δ(1013/74), were constructed as follows (details of the construction are illustrated diagramatically in FIG. 2). Each of the plasmids have inserts with 5' promoters digested in the 5'→3' direction, prepared in a manner similar to that described in Example 1-4. Because the length of the digested fragment cannot be accurately predicted after digestion with exonuclease III, each plasmid contains a promoter of different length.

1) Construction of pSCA1013-Δ(1013/320)

pSCA213 was derived from pSCA111 DNA by a procedure similar to that described in Example 1-4 (See FIG. 2). pSCA213 DNA was digested with EcoRI and HindIII, and the products of the digestion were electrophoresed on a 1% w/v agarose gel, and an EcoRI-HindIII DNA fragment of approximately 2.1 kbp, containing the P-450$_{sca-2}$ gene and a region of the 5' promoter, was excised from the gel. The excised DNA was treated with phenol-chloroform and recovered from the aqueous layer using ethanol precipitation, and the precipitated DNA was dried under reduced pressure.

100 ng of pSCA301 was digested with EcoRI and HindIII, and prepared as described in Example 1–6. This DNA was added to approximately 200 ng of the 2.1 kbp EcoRI-HindIII fragment obtained above in ligase buffer containing 1800 units of T4 DNA ligase to a final volume 100 μl, and the reaction was allowed to proceed for 2 hours at 16° C. After this time, the ligated DNA was transformed into *Streptomyces lividans*, as described in method [1] above. The thiostrepton-resistant *Streptomyces lividans* strain obtained by this procedure was named TK21/pSCA1013-Δ(1013/320). Plasmid DNA was obtained from this strain by method [2] above, and this plasmid was named pSCA1013-Δ(1013/320).

2) Construction of pSCA1013-Δ(1013/158)

Figure 2:
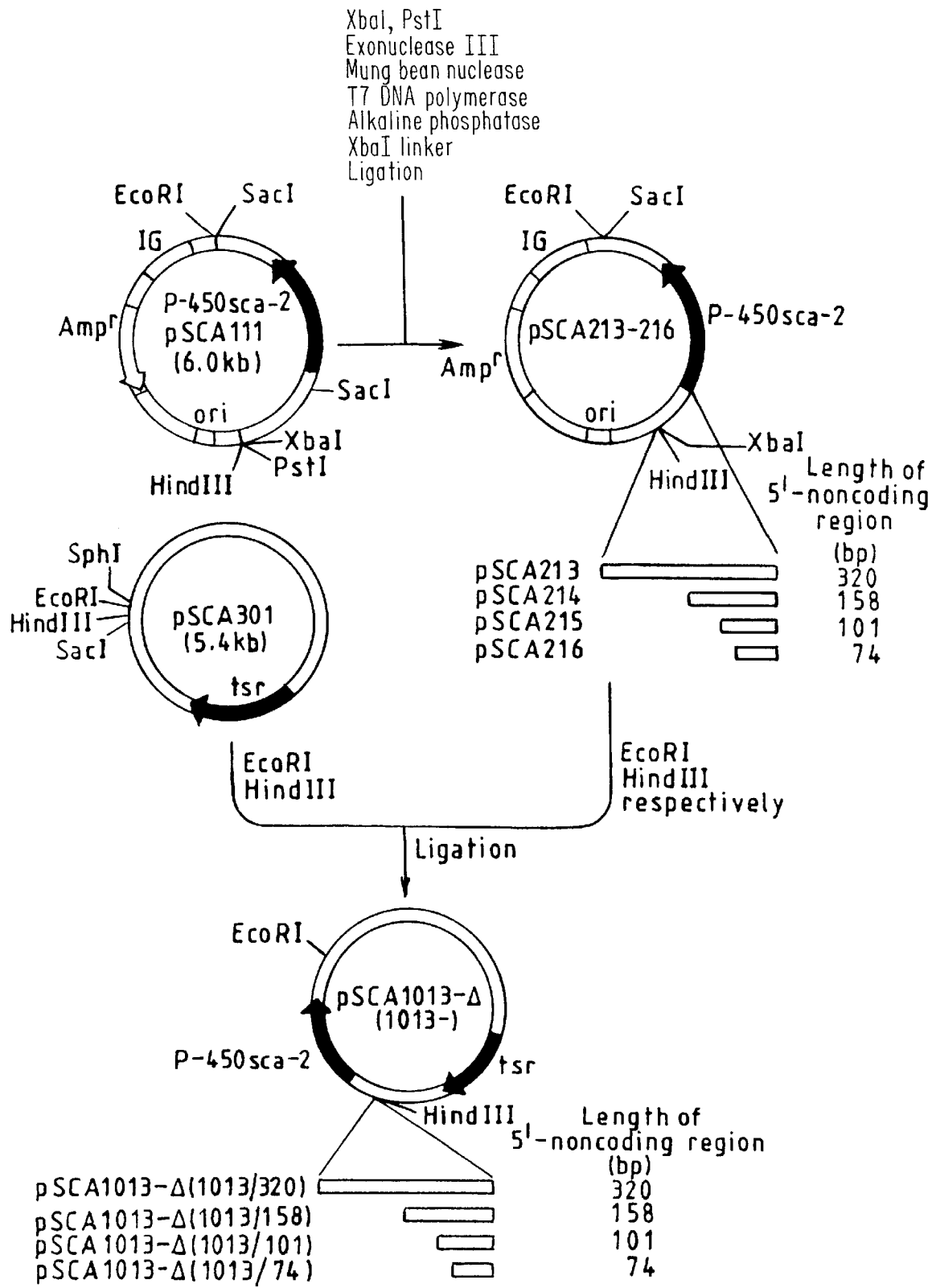
FIG. 2 is a plan for the construction of plasmids containing 320, 158, 101 and 74 bp promoters of the invention [pSCA1013-Δ(1013/320), pSCA1013-Δ(1013/158), pSCA1013-Δ(1013/101) and pSCA1013-Δ(1013/74), respectively] obtained from the 3' end of the 5'-noncoding region of the P-450$_{sca-2}$ gene.

Plasmid pSCA214 was derived from pSCA111 DNA by a procedure similar to that described in Example 1-4 (See FIG. 2). In a manner similar to that of 1) above, pSCA214 was digested with EcoRI and HindIII to obtain an EcoRI-HindIII DNA fragment of approximately 1.93 kbp length containing the P-450$_{sca-2}$ gene and a region of the 5' promoter. This fragment was used to transform pSCA301 as described in 1) above.

The thiostrepton-resistant *Streptomyces lividans* strain obtained was named TK21/pSCA1013-Δ(1013/158). Plasmid DNA was obtained from this strain by method [2] above, and this plasmid was named pSCA1013-Δ(1013/158).

3) Construction of plasmid pSCA1013-Δ(1013/101)

Plasmid pSCA215 was derived from pSCA111 DNA by a procedure similar to that described in Example 1-4 (See FIG. 2). In a manner similar to that of 1) above, pSCA215 was digested with EcoRI and HindIII to obtain an EcoRI-HindIII DNA fragment of approximately 1.87 kbp length containing the P-450$_{sca-2}$ gene and a region of the 5' promoter. This fragment was used to transform pSCA301 as described in 1) above.

The thiostrepton-resistant *Streptomyces lividans* strain obtained was named TK21/pSCA1013-Δ(1013/101). Plasmid DNA was obtained from this strain by method [2] above, and this plasmid was named pSCA1013-Δ(1013/101).

4) Construction of pSCA1013-Δ(1013/74)

Plasmid pSCA216 was derived from pSCA111 DNA by a procedure similar to that described in Example 1-4 (See FIG. 2). In a manner similar to that of 1) above, pSCA216 was digested with EcoRI and HindIII to obtain an EcoRI-HindIII DNA fragment of approximately 1.85 kbp length containing the P-450$_{sca-2}$ gene and a region of the 5' promoter. This fragment was used to transform pSCA301 as described in 1) above.

The thiostrepton-resistant *Streptomyces lividans* strain obtained was named TK21/pSCA1013-Δ(1013/74). Plasmid DNA was obtained from this strain by method [2] above, and this plasmid was named pSCA1013-Δ(1013/74).

5) Determination of the Size and Nucleotide Sequence of Promoter Fragments

The length of the 5' promoter fragments present in each of the plasmids pSCA1013-Δ(1013/320), pSCA1013-Δ(1013/158), pSCA1013-Δ(1013/101) and pSCA1013-Δ(1013/74) was determined in accordance with the method described in Example 2.

In plasmid pSCA1013-Δ(1013/320), the DNA 5' to the coding region of P-450$_{sca-2}$ was shown to be 320 bp in length, corresponding to nucleotide nos. 109–428 of SEQ ID NO. 1.

In plasmid pSCA1013-Δ(1013/158), the DNA 5' to the coding region of P-450$_{sca-2}$ was shown to be 158 bp in length, corresponding to nucleotide nos. 271–428 of SEQ ID NO. 1.

In plasmid pSCA1013-Δ(1013/101), the DNA 5' to the coding region of P-450$_{sca-2}$ was shown to be 101 bp in length, corresponding to nucleotide nos. 328–428 of SEQ ID NO. 1.

In plasmid pSCA1013-Δ(1013/74), the DNA 5' to the coding region of P-450$_{sca-2}$ was shown to be 74 bp in length, corresponding to nucleotide nos. 355–428 of SEQ ID NO. 1.

6) Plasmid-mediated Production of Pravastatin Sodium

Production of pravastatin sodium was measured according to the method described in Example 3 for the following strains; *Streptomyces lividans* TK 21/pSCA1013-Δ(1013/320), *Streptomyces lividans* TK 21/pSCA1013-Δ(1013/158), *Streptomyces lividans* TK 21/pSCA1013-Δ(1013/101), and *Streptomyces lividans* TK21/pSCA1013-Δ(1013/74). *Streptomyces lividans* strain TK 21 was used as a control. The results are shown in Table 1.

TABLE 1

| S. lividans strain | pravastatin sodium (μg/ml) |
|---|---|
| TK21/pSCA1013-Δ(1013/320) | 52 |
| TK21/pSCA1013-Δ(1013/158) | 12 |
| TK21/pSCA1013-Δ(1013/101) | 17 |
| TK21/pSCA1013-Δ(1013/74) | 16 |
| TK21 | 0 |

Thus, it can be seen that all of the 5' promoters of the plasmids prepared in this example exhibit useful promoter activity.

EXAMPLE 5

Transcription Induction by ML-236B as Measured by Northern Blotting i) Preparation of Total RNA The following strains of *S. lividans*, that is *S. lividans* TK21/pSCA205, *S. lividans* TK21/pSCA1013-Δ(1013/428), *S. lividans* TK21/pSCA1013-Δ(1013/320), *S. lividans* TK21/pSCA1013-Δ(1013/158), *S. lividans* TK21/pSCA1013-Δ(1013/101) and *S. lividans* TK21/pSCA1013-Δ(1013/74) were cultured in a manner similar to that described in Example 3.

As in Example 3, ML-236B sodium was added to the culture to a final concentration of 500 μg/ml for the test experiments. The control, or negative experiments, were prepared in the same manner, but without the addition of ML-236B. At this stage, after addition of ML-236B to the test experiments, culturing was continued at 28° C. and 200 rpm for one hour. After this time, the culture medium was centrifuged at 4° C. and 4,000×g for 10 minutes and the pellets were frozen immediately in liquid nitrogen and kept at temperatures below −80° C.

Three grams of each frozen pellet were ground into powder in a mortar previously cooled over dry ice. This powder was then placed into a centrifugation tube filled with 15 ml of guanidinethiocyanate solution [4M of guanidinethiocyanate (Fluka), 4% (w/v) of Sarcosyl(Sigma), 0.1% (w/v) of Antifoam A (Sigma), 20 mM of EDTA-2sodium, 4 mM of 2-mercaptoethanol and 25 mM of citric acid 3 sodium (pH 7.0)], and vigorously stirred. The cell debris was then homogenized for 30 minutes using a polytron-homogenizer. This homogenate was then centrifuged at 9,000 rpm (10,000×g) and 4° C. for 15 minutes. The supernatants thus obtained were again centrifuged at 9,000 rpm (10,000×g) and 4° C. for 15 minutes. Seven ml of each resulting supernatant fraction were then layered softly on 3 ml of 5.7M cesium chloride solution containing 0.1M EDTA-2 sodium which had previously been placed in an ultracentrifugation tube (13 PA: Hitachi Koki Co., Ltd) and centrifuged at 4° C. and 30,000 (40000×g) for 15 hours. After this time, the resulting pellet was dissolved in 0.3 ml of 10 mM Tris-HCl buffer (pH 8.0) containing 1 mM EDTA.2 sodium ("TE buffer") and 30 ml of 3M acetic acid/acetic acid sodium buffer (pH 5.2) and 1 ml of ethanol were then added to the resulting preparation. This preparation was then centrifuged at 14500 rpm (18,000×g) and 4° C. for 5 minutes. The pellet was dried under reduced pressure and dissolved in 40 μl of TE buffer to be used as a total RNA sample in subsequent stages.

ii) Preparation of Probe

Ten μg of pSCA205 were digested with 100 units of PvuII at 37° C. for 3 hours in H buffer, and electrophoresed on a 1% w/v agarose gel to excise a 0.49 kbp PvuII fragment. The resulting DNA fragment purified using phenol-chloroform and the DNA was precipitated with ethanol, and dried under reduced pressure. 500 ng of this DNA fragment was labelled with $^{32}$P-dCTP (6000 Ci/mmole) using a nick translation kit (Amersham). The resulting PvuII-labelled fragment (0.49 kbp) was precipitated with ethanol twice to remove any unreacted $^{32}$P-dCTP. The resulting probe was dissolved in 400 ml of TE buffer and kept below −20° C.

iii) Northern Hybridization

Ten μg of each total RNA was electrophoresed on a 1.2% w/v agarose gel at 100 V for 4 hours in 20 mM MOPS buffer (Sigma) containing 0.92M formaldehyde, 8 mM acetic acid sodium and 1 mM EDTA (pH 7.0). After this time, the gel was shaken gently in 0.1M ammonium acetate. The gel was then shaken for one hour in 50 mM Tris-HCl buffer (pH 8.0) containing 1M ammonium acetate. The total RNA was transferred to Nylon-Membrane (PALL Ultrafiltration Corp.) and fixed by standard methods. The Nylon-Membrane was then placed in 30 ml of 5×SSPE (180 mM of sodium chloride, 0.1 mM of EDTA.2 sodium, 18.6 mM of dihydro-sodium phosphate.2 H$_2$O and 101 mM of hydrodisodium phosphate.12H$_2$O) containing 50% v/v formamide, 2.5×Denhart solution [0.2 g/l of Bovine Serum Albumin, 0.2 g/l of Ficol 400 (Pharmacia) and 0.2 g/l of Polyvinyl pyrrolidone] and 100 μg/ml salmon sperm DNA at 42° C. for 4 hours. The Nylon-Membrane was then reacted with 100 μl of the labelled DNA fragment prepared above (0.49 kbp), encoding part of the P-450$_{sca-2}$, at 42° C. overnight in 30 ml of 5×SSPE containing 50% v/v formamide, 1×Denhart solution, 100 μg/ml of salmon sperm DNA and 0.1% v/v SDS. After this procedure, the Nylon-Membrane was then washed twice in 2×SSPE containing 0.1% w/v SDS for 5 minutes at room temperature, and then washed again in 1×SSPE containing 0.1% SDS v/v at 55° C. for 10 minutes and then, finally, washed in 0.1×SSPE containing 0.1% SDS v/v at 55° C. for 15 minutes. The membrane was then dried and the comparative production of 1.8 kbp of MRNA transcribed from the P-450$_{sca-2}$ gene was measured using the Image-Analyzer BA 100 (Fuji film). The values obtained from negative control for S. lividans TK21/pSCA205 was defined as 1, the values for other results being evaluated accordingly. The results are shown in table 2 below.

TABLE 2

|  | ML-236B sodium | |
| --- | --- | --- |
|  | absent | present |
| S. lividans TK21/pSCA205 | 1.0 | 26 |
| S. lividans TK21/pSCA1013-Δ(1013/428) | 31 | 32 |
| S. lividans TK21/pSCA1013-Δ(1013/320) | 36 | 31 |

TABLE 2-continued

|  | ML-236B sodium | |
| --- | --- | --- |
|  | absent | present |
| S. lividans TK21/pSCA1013-Δ(1013/158) | 4.8 | 8.9 |
| S. lividans TK21/pSCA1013-Δ(1013/101) | 7.6 | 15 |
| S. lividans TK21/pSCA1013-Δ(1013/74) | 2.2 | 1.3 |

From the above, it can clearly be seen that the promoter activity of the intact 5' noncoding region (1 kbp) is dependent on induction by ML-236B sodium (S. lividans TK21/pSCA205). By contrast, the promoters of the invention require no such induction. It will also be appreciated that the present Example assays levels of transcription, levels of expression necessarily lagging behind transcription.

What is claimed is:

1. A recombinant DNA having transcription promoter activity, said DNA is a part of, but not all of a 1 kbp 5'-noncoding region immediately adjacent to an open reading frame of *Streptomyces carbophilus*, said open reading frame encoding a P-450 cytochrome.

2. The DNA of claim 1, which has transcription promoter activity in at least one strain of *Streptomyces carbophilus*.

3. The DNA of claim 1, which has transcription promoter activity in at least one strain of *Streptomyces lividans*.

4. The DNA of claim 1, wherein said P-450 cytochrome is the P-450$_{sca-2}$ cytochrome.

5. A host transformed with a vector containing the DNA of claim 4, said DNA being in operative transcription promoter linkage with a further open reading frame.

6. The DNA of claim 1, wherein said promoter activity is constitutive.

7. A host transformed with a vector containing the DNA of claim 6, said DNA being in operative transcription promoter linkage with a further open reading frame.

8. The DNA of claim 1, wherein said DNA is at least 74 bp long.

9. The DNA of claim 1, wherein said DNA is at least 300 bp long.

10. A host transformed with a vector containing the DNA of claim 9, said DNA being in operative transcription promoter linkage with a further open reading frame.

11. The DNA of claim 1, which has a length of less than 100 bp.

12. The DNA of claim 1, which is directly equivalent to said 1 kbp 5'-noncoding region which has had at least one base pair removed.

13. The DNA of claim 12, wherein said at least one base pair is removed by means selected from the group consisting of restriction endonucleases, engineering, digestion from an end of said 5'-noncoding region, and combinations thereof.

14. The DNA of claim 1, which is directly equivalent to said 1 kbp 5'-noncoding region which has been partially digested in the 5'→3' direction.

15. The DNA of claim 1 which is double stranded.

16. A DNA strand which is a single strand of the DNA of claim 12.

17. The DNA of claim 1, comprising a continuous sequence of the sequence of SEQ ID. No. 1, starting from 428 and continuing all or part of the way to base number 1.

18. A host transformed with a vector containing the DNA of claim 17, said DNA being in operative transcription promoter linkage with a further open reading frame.

19. The DNA of claim 1, which has a length sufficient for exhibiting promoter activity of a DNA insert selected from the group consisting of the 320 bp insert of the plasmid pSCA1013-Δ(1013/320) and the 428 bp DNA insert of the plasmid pSCA1013-Δ(1013/428).

20. A host transformed with a vector containing the DNA of claim 19, said DNA being in operative transcription promoter linkage with a further open reading frame.

21. The DNA of claim 1 which is sufficiently short that it is not subject to a significant level of substrate induction.

22. The DNA of claim 1 having an overall sequence which is identical to a sequence of said 1 kbp 5'-noncoding region.

23. The DNA of claim 1 having an overall sequence which shares sequence homology with at least one sequence of bases of said 1 kbp 5'-noncoding region.

24. The DNA of claim 1 which hybridizes at 60° C. in 6×SSC with DNA comprising the nucleotide sequence 1 to 428 of SEQ ID NO. 1.

25. The DNA of claim 1 which hybridizes at 60° C. in 6×SSC with DNA comprising the nucleotide sequence 1 to 320 of SEQ ID NO. 1.

26. The DNA of claim 1, which exhibits sufficient promoter activity to ensure a total level of expression higher after a period of one hour than compared with the total level of expression obtained with said 1 kbp 5'-noncoding region which has been subject to one hour of substrate induction.

27. The DNA of claim 1 having one or more additional base pairs linked in tandem thereto at at least one end thereof.

28. The DNA of claim 1 which has the nucleotide sequence 1 to 428 of SEQ ID NO. 1.

29. A host transformed with a vector containing the DNA of claim 28, said DNA being in operative transcription promoter linkage with a further open reading frame.

30. The DNA of claim 1, which has the nucleotide sequence 1 to 320 of SEQ ID NO. 1.

31. A host transformed with a vector containing the DNA of claim 30, said DNA being in operative transcription promoter linkage with a further open reading frame.

32. The DNA of claim 1, which has the nucleotide sequence 1 to 158 of SEQ ID NO. 1.

33. The DNA of claim 1, which has the nucleotide sequence 1 to 101 of SEQ ID NO. 1.

34. The DNA of claim 1, which has the nucleotide sequence 1 to 74 of SEQ ID NO. 1.

35. The DNA of claim 1 when obtained from *Streptomyces lividans* SANK 62795 having the accession number FERM BP-5299.

36. A host transformed with a vector containing the DNA of claim 35, said DNA being in operative transcription promoter linkage with a further open reading frame.

37. The DNA of claim 1, in operative transcription promoter linkage with an open reading frame.

38. A DNA sequence comprising the DNA of claim 1, provided that the DNA of claim 1 is not comprised in said DNA sequence in such a way as to provide a complete version of said 1 kbp 5'-noncoding region.

39. The DNA of claim 1, wherein at least one base pair is removed from said 1 kbp 5'-noncoding region.

40. A vector containing DNA having transcription promoter activity, said DNA is a part of, but not all of a 1 kbp 5'-noncoding region immediately adjacent to an open reading frame of *Streptomyces carbophilus*, said open reading frame encoding a P-450 cytochrome.

41. The vector of claim 40, wherein said DNA has transcription promoter activity in at least one strain of *Streptomyces carbophilus*.

42. The vector of claim 40, wherein said DNA has transcription promoter activity in at least one strain of *Streptomyces lividans*.

43. The vector of claim 40, wherein said DNA is in operative transcription promoter linkage with an open reading frame.

44. The vector of claim 40, wherein said vector expresses a protein encoded by said open reading frame in an appropriate host cell.

45. The vector of claim 44, wherein said protein is cytochrome P-450$_{sca-2}$.

46. The vector of claim 40, which confers a selectable phenotype on the host.

47. A host transformed with a vector containing DNA having transcription promoter activity, said DNA is a part of, but not all of a 1 kbp 5'-noncoding region immediately adjacent to an open reading frame of *Streptomyces carbophilus*, said open reading frame encoding a P-450 cytochrome, said DNA being in operative transcription promoter linkage with a further open reading frame.

48. The host of claim 47, wherein said DNA in said vector has transcription promoter activity in at least one strain of *Streptomyces carbophilus*.

49. The host of claim 47, wherein said DNA in said vector has transcription promoter activity in at least one strain of *Streptomyces lividans*.

50. An expression system comprising the host of claim 47 and which expresses a protein encoded by said further open reading frame when said host is cultured under conditions to express said protein.

51. The expression system of claim 50, wherein said host is a prokaryote host.

52. The expression system of claim 50, wherein said host is selected from the group consisting of *Escherichia coli*, *Bacillus subtilis* and Streptomyces spp.

53. The expression system of claim 50, wherein said host is an actinomycete host.

54. The expression system of claim 50, wherein said host is a streptomycete host.

55. The expression system of claim 50, wherein said host is *Streptomyces lividans*.

56. The expression system of claim 50, wherein said host is *Streptomyces lividans* strain TK21.

57. The expression system of claim 50, wherein said host is a transformed strain of *S. lividans*, and the open reading frame is heterologous DNA.

58. The expression system of claim 50, for expressing prokaryotic proteins.

59. The expression system of claim 50, wherein said expression vector is a multicopy plasmid.

60. The expression system of claim 59, wherein said multicopy plasmid is pIJ702.

61. The expression system of claim 50, for the expression of products which are naturally only expressed after substrate induction.

62. A method for the production of an antibiotic, said method comprising culturing the expression system of claim 50, said further open reading frame encoding an antibiotic.

63. The expression system of claim 50, which is co-cultured with a system producing a substrate for said P-450 cytochrome.

64. The expression system of claim 50, wherein the protein to be expressed is a P-450 cytochrome.

65. The expression system of claim 50, wherein the protein to be expressed is a P-450$_{sca}$ cytochrome.

66. The expression system of claim 50, wherein the protein to be expressed is P-450$_{sca-2}$ cytochrome.

67. The expression system of claim 50, wherein the protein to be expressed is a P-450$_{sca}$ cytochrome and the host is a strain of *S. lividans* which also expresses an electron transfer system enabling said cytochrome to take part in the hydroxylation of any ML-236B present in the system.

68. The expression system of claim 67, wherein said P-450$_{sca}$ cytochrome is P-450$_{sca-2}$.

69. A process for producing pravastatin sodium which comprises culturing the expression system of claim 50 in a medium containing ML-236B, wherein the protein to be expressed is P-450$_{sca-2}$ cytochrome and the host is *S. lividans* strain TK21 which also expresses an electron transfer system enabling said cytochrome to hydroxylate ML-236B sodium, said culturing being under conditions allowing the production of cytochrome P-450$_{sca-2}$, allowing said ML-236B sodium to be converted to pravastatin sodium by the catalytic action of said cytochrome P-450$_{sca-2}$, and then recovering the pravastatin sodium from the culture.

70. The process of claim 69, wherein said host is *Streptomyces lividans* SANK 62795 having the accession number FERM BP-5299.

71. The process of claim 69, wherein said ML-236B is produced by *Penicillium citrinum* which is co-cultivated with said host.

72. The expression system of claim 50, wherein said open reading frame encodes an amino acid sequence.

73. The expression system of claim 72, wherein said amino acid sequence is selected from the group consisting of a natural form of a protein, a variant form of a protein, a polymer form of a protein, a fused form of two or more different proteins and combinations thereof.

74. An isolated expression product of the expression system of claim 50.

75. The expression product of claim 50, which is P-450$_{sca}$.

76. A process for producing a desired protein, said process comprising culturing the transformed host of claim 47 under conditions permitting production of said protein in order to produce the protein, and recovering the protein.

77. *Streptomyces lividans* SANK 62795 having the accession number FERM BP-5299.

78. The plasmid pSCA1013-Δ(1013/428).
79. The plasmid pSCA1013-Δ(1013/320).
80. The plasmid pSCA1013-Δ(1013/158).
81. The plasmid pSCA1013-Δ(1013/101).
82. The plasmid pSCA1013-Δ(1013/74).
83. *Streptomyces lividans* TK 21/pSCA1013-Δ(1013/428).
84. *Streptomyces lividans* TK 21/pSCA1013-Δ(1013/320).
85. *Streptomyces lividans* TK 21/pSCA1013-Δ(1013/158).
86. *Streptomyces lividans* TK 21/pSCA1013-Δ(1013/101).
87. *Streptomyces lividans* TK21/pSCA1013-Δ(1013/74).

88. A transcription promoter having the nucleotide sequence 1 to 428 of SEQ ID NO. 1 obtained by culturing *Streptomyces lividans* SANK 62795 having accession number FERM BP-5299, recovering pSCA1013-Δ(1013/428) from the cells and digesting the plasmid with restriction enzymes.

* * * * *

UNITED STATES PATENT AND TRADEMARK OFFICE
CERTIFICATE OF CORRECTION

PATENT NO. : 5,830,695
DATED : November 3, 1998
INVENTOR(S) : Serizawa et al.

It is certified that error appears in the above-identified patent and that said Letters Patent is hereby corrected as shown below:

Title page,
Item [73], Assignee, delete "Sankto" and insert -- Sankyo --.

Column 32, claim 16,
Line 29, delete "12" and insert -- 15 --.

Column 32, claim 27,
Line 61, delete "at" second occurrence.

Signed and Sealed this

Sixteenth Day of April, 2002

Attest:

JAMES E. ROGAN
Attesting Officer     Director of the United States Patent and Trademark Office

UNITED STATES PATENT AND TRADEMARK OFFICE
CERTIFICATE OF CORRECTION

PATENT NO.    : 5,830,695
DATED         : November 3, 1998
INVENTOR(S)   : Nobufusa Serizawa et al.

It is certified that error appears in the above-identified patent and that said Letters Patent is hereby corrected as shown below:

Column 32,
Lines 54 and 55, replace "nucleotide sequence 1 to 320 of SEQ ID NO. 1" with
-- nucleotide sequence 109 to 428 of SEQ ID NO. 1 --;

Column 33,
Line 2, replace "nucleotide sequence 1 to 320 of SEQ ID NO. 1" with -- nucleotide sequence 109 to 428 of SEQ ID NO. 1 --;
Line 7, replace "nucleotide sequence 1 to 158 of SEQ ID NO. 1" with -- nucleotide sequence 271 to 428 of SEQ ID NO. 1 --;
Line 9, replace "nucleotide sequence 1 to 101 of SEQ ID NO. 1" with -- nucleotide sequence 328 to 428 of SEQ ID NO. 1 --;
Line 11, replace "nucleotide sequence 1 to 74 of SEQ ID NO. 1" with -- nucleotide sequence 355 to 428 of SEQ ID NO. 1 --;

Signed and Sealed this

Sixth Day of April, 2004

JON W. DUDAS
*Acting Director of the United States Patent and Trademark Office*

SEQUENCE LISTING ( 1 ) GENERAL INFORMATION:

( i i i ) NUMBER OF SEQUENCES: 3

( 2 ) INFORMATION FOR SEQ ID NO: 1:

( i ) SEQUENCE CHARACTERISTICS:
        ( A ) LENGTH: 428 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Streptomyces carbophilus
        ( B ) STRAIN: SANK 62585

( x i ) SEQUENCE DESCRIPTION: SEQ ID NO: 1:

```
CAGCAGGACC   AGGACGTCGC   CGCGCAGTTC   GCCGGTATCG   GGGAGGTCGA   CCTCGGAGAT      60

CTTCCCCAAC   CGGCAGGCGT   CGACCACGAG   TTGGGCCCGG   CTCGGCCACC   TGCGGTAGAC     120

CGCCGCCTTT   CCCGTGCGGG   CCCGGACCGC   CACCCGCTCC   ATGGTGAGCG   AGGCGTAACC     180

CACCTCGCCG   AGCTCGTCCA   AAGTCGCCAG   CAGAATGGCG   CTTTCCAGTT   CCTCGCCGCG     240

ACGACGCGGG   CCTTTGCGGT   GGTCAAGGGG   TGGTTCGGTG   GCCGGTTCCG   TGGCCGGTTC     300

GGCACTGTTG   GGCACCCCTG   CCTCCCGTGT   CTGTCGCATA   GGGGCCGTTG   CGTTCTTCCG     360

GGTGGACAGC   CTAGCCTCCA   ACTTAGAGAA   CAGTCCGTTC   TTTAACGTCT   GAGGTTTCGA     420

GGGTTTCG                                                                     428
```

( 2 ) INFORMATION FOR SEQ ID NO: 2:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: other nucleic acid -continued (A) DESCRIPTION: /desc = "Synthetic DNA"

(iii) HYPOTHETICAL: NO (iv) ANTI-SENSE: NO (xi) SEQUENCE DESCRIPTION: SEQ ID NO: 2:

GATCTAAGCT TGAATTCGCA TG                                                                                              22

(2) INFORMATION FOR SEQ ID NO: 3:

(i) SEQUENCE CHARACTERISTICS:
   (A) LENGTH: 14 base pairs
   (B) TYPE: nucleic acid
   (C) STRANDEDNESS: single
   (D) TOPOLOGY: linear (ii) MOLECULE TYPE: other nucleic acid
   (A) DESCRIPTION: /desc = "Synthetic DNA"

(iii) HYPOTHETICAL: NO (iv) ANTI-SENSE: NO (xi) SEQUENCE DESCRIPTION: SEQ ID NO: 3:

CGAATTCAAG CTTA                                                                                                       14